United States Patent
Mulrooney et al.

(10) Patent No.: US 7,001,726 B1
(45) Date of Patent: Feb. 21, 2006

(54) ENZYMATICALLY CATALYSED SIGNAL AMPLIFICATION

(75) Inventors: Conor Mulrooney, Stockport (GB); John Douglas Oultram, Stretford (GB)

(73) Assignee: Tepnel Medical Limited, (GB)

( * ) Notice: Subject to any disclaimer, the term of this patent is extended or adjusted under 35 U.S.C. 154(b) by 0 days.

(21) Appl. No.: 09/936,382

(22) PCT Filed: Mar. 13, 2000

(86) PCT No.: PCT/GB00/00921

§ 371 (c)(1),
(2), (4) Date: Sep. 10, 2001

(87) PCT Pub. No.: WO00/55365

PCT Pub. Date: Sep. 21, 2000

(30) Foreign Application Priority Data

Mar. 12, 1999 (GB) .................................. 9905580

(51) Int. Cl.
*C12Q 1/68* (2006.01)
*C12P 19/34* (2006.01)
*C07H 21/04* (2006.01)

(52) U.S. Cl. ................. 435/6; 435/91.1; 435/91.2; 536/23.1; 536/24.3; 536/24.33

(58) Field of Classification Search .............. 435/6, 435/91.1, 91.2; 536/23.1, 24.3, 24.32, 24.33
See application file for complete search history.

(56) References Cited

U.S. PATENT DOCUMENTS 5,451,503 A   9/1995   Hogan et al.
5,681,697 A   10/1997  Urdea et al.

FOREIGN PATENT DOCUMENTS

WO   WO97/42346    11/1997
WO   WO98/02580    1/1998
WO   WO 98/02580 * 1/1998

* cited by examiner

*Primary Examiner*—Kenneth R. Horlick
*Assistant Examiner*—Cynthia Wilder
(74) *Attorney, Agent, or Firm*—Wallenstein Wagner & Rockey, Ltd.

(57) ABSTRACT

The present invention concerns detection of target molecules using methods of enzymatically catalysed amplification of target associated detectable structures.

79 Claims, 21 Drawing Sheets

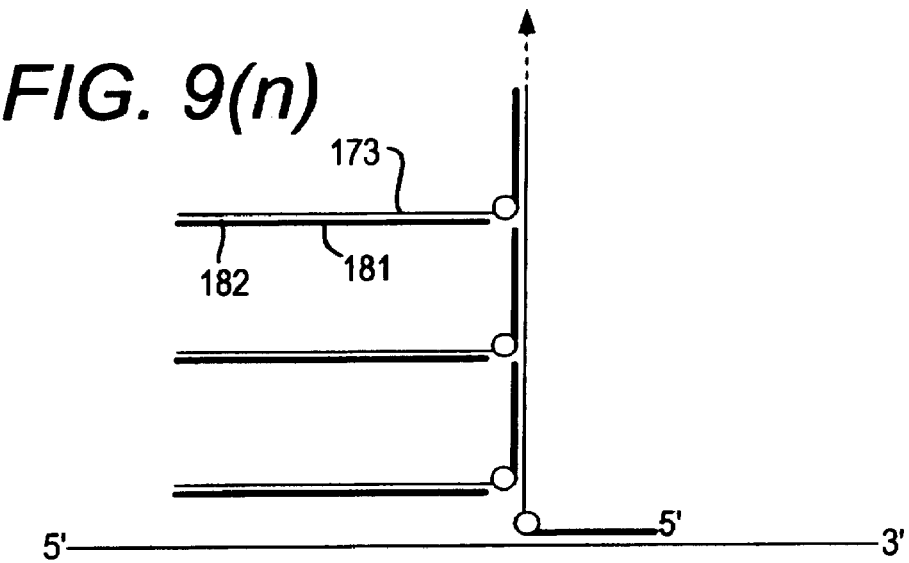
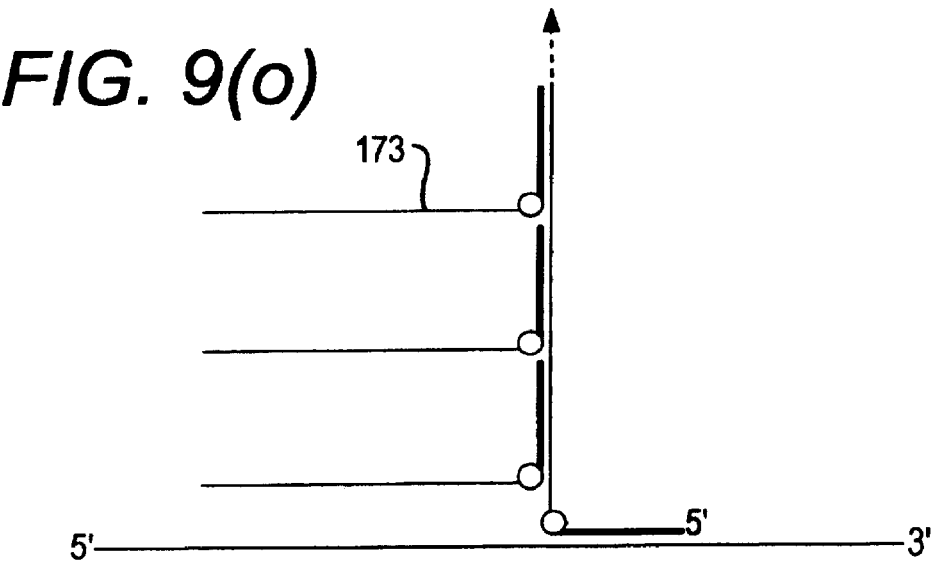

ENZYMATICALLY CATALYSED SIGNAL AMPLIFICATION

This Application is a U.S. National filing under §371 of International Application No. PCT/GB00/00921, filed Mar. 13, 2000, claiming priority from British Appln. No. 9905580.8, filed Mar. 12, 1999, now pending (which is hereby incorporated by reference).

FIELD OF THE INVENTION

The present invention concerns detection of target molecules using methods of enzymatically catalyzed amplification of target associated detectable structures.

BACKGROUND OF THE INVENTION

Several nucleic acid amplification techniques are already known, e.g. the Polymerase Chain Reaction (PCR). However many of these techniques (including PCR) suffer from the disadvantage that they specifically amplify a target sequence (amplicon) present within the sample of interest. This amplicon, once generated, can easily contaminate a laboratory working area in which strict controls are not maintained. Such contamination can render subsequent amplification reactions suspect, and can require a cessation of testing and the initiation of expensive decontamination procedures.

Techniques such as PCR, which detect the presence of a sequence by amplifying its number to detectable levels, are known as Target Amplification systems. In contrast, several techniques are known which amplify a signal to detectable levels, usually following the binding of a detector molecule to the molecule of interest, without amplification of said molecule. These are referred to as Signal Amplification techniques.

One such system Chiron Corporation (Urdeaet al., U.S. Pat. No. 5,681,697 and references cited therein) is known as the branched DNA system (bDNA). This system relies on the binding to the target molecule, of a large number of detector probes, which contain within their sequence a site for hybridisation of a non-target specific sequence. This sequence acts as the site for hybridisation of a pre-synthesized branched DNA structure with numerous sites for the hybridisation of secondary branches or of detection probes. One of the main disadvantages of this system is the large number of components required to generate the final structure to which the detection probes adhere. In addition, the many hybridisation steps involved in the assembly process render the system susceptible to the production of non-specific background signal.

Other target detection systems known in the art include U.S. Pat. No. 5,451,503, WO 98/02580. WO 97/42346 and U.S. Pat. No. 5,681,697.

SUMMARY OF THE INVENTION

The current invention outlines a method for the amplification of a nucleic acid based signal. It involves the generation of a repeating structure containing multiple copies of a detectable sequence, and is produced through the concerted action of a polymerase (which extends the repeating structure) and a separating agent (which uncovers hybridisation sites to allow assembly of sequence repeats). The method of the invention offers the following advantages over methods existing in the art:

1. It uses a small number of inexpensive components and so avoids the high cost per assay problems associated with other signal amplification systems such as bDNA.
2. It uses a signal amplification rather than a target amplification approach and thus it overcomes contamination problems associated with many current methodologies such as PCR.
3. It is an enzymatically catalyzed process that actively assembles the signal generating structure rather than relying on the passive hybridisation-based approaches of non-enzymatic methods such as bDNA.
4. It has the ability to address RNA and DNA targets with equal efficiency without pre-treatments, unlike for example PCR which requires an initial reverse transcription step before RNA targets can be amplified.
5. As the process is used in conjunction with a solid phase immobilized target it has the potential to be integrated into 'cutting edge' solid phase devices such as Biochips.

The target molecule may first be immobilized on a solid phase before employing the detection method of the present invention. The invention is not limited to this or any other specific assay format.

DETAILED DESCRIPTION OF THE INVENTION

According to a first embodiment of the present invention there is provided a method for detecting a target molecule, comprising the steps of:
i) contacting a sample with a locator probe comprising a binding moiety specific for said target molecule and an amplification nucleic acid sequence to produce a target molecule-locator probe complex;
ii) producing an amplification structure bound to any complex produced in the preceding step by performing one or more times the amplification step of treating said sample and locator probe with:
  a) a single stranded amplification template comprising:
    i) arranged in a 5' to 3' direction:
      a) an extension nucleic acid sequence;
      b) a hybridisation nucleic acid sequence complementary to the amplification nucleic acid sequence of the previous amplification step or, where there is no previous amplification step, of the preceding step and having substantially the same sequence as said extension nucleic acid sequence; and
      c) an amplification moiety, being limited in all but the final repeat to a nucleic acid sequence; and
    ii) optionally comprising at least one signal moiety being other than a nucleic acid sequence.
  b) a polymerising agent capable of extending the 3' terminus of the amplification nucleic acid sequence of the previous amplification step or, where there is no previous amplification step, of the preceding step by synthesising a complementary strand to said extension nucleic acid sequence of said amplification template;
  c) a separating agent capable of removing sufficient of said extension nucleic acid sequence of said amplification template when hybridised to said complementary strand to allow subsequent hybridisation of said hybridisation nucleic acid sequence of said amplification template to said complementary strand; and
  d) the reagents and conditions necessary to effect the action of said polymerising agent and separating agent to allow the extension of the 3' terminus of the amplification nucleic acid sequence of the previous amplification step or, where there is no previous amplification step, of the preceding step by the synthesis of a plurality of sequences complementary to said extension nucleic acid sequence of said amplification template;

iii) detecting any bound amplification template from the amplification step or steps; and iv) correlating the results of detection step (iii) with the presence of said target molecule.

Reference in the various embodiments of the invention to "the preceding step" is typically reference to step (i) of the method, although it does include (see below) as a "preceding step" an amplification step (i.e. a step of producing an amplification structure) of a different embodiment of the invention.

The removal of said extension nucleic acid sequence may be achieved by the use of a 5' double stranded exonuclease against whose activity the hybridisation nucleic acid sequence is protected. The hybridisation nucleic acid sequence (and other sequences, as necessary) may be protected from exonuclease activity by substituting 2'-O-methyl RNA residues for normal residues during its synthesis.

In a second embodiment, the present invention provides a method for detecting a target molecule (using amplification templates whose extension and hybridisation regions differ so as to minimize interfering side reactions) comprising the steps of:

i) contacting a sample with a locator probe comprising a binding moiety specific for said target molecule and an amplification nucleic acid sequence to produce a target molecule-locator probe complex;

ii) producing an amplification structure bound to any complex produced in the preceding step by performing one or more times the amplification step of treating said sample and locator probe with:

a) a single stranded first amplification template comprising:
  i) arranged in a 5' to 3' direction:
    a) an extension nucleic acid sequence;
    b) a hybridisation nucleic acid sequence complementary to the amplification nucleic acid sequence of the previous amplification step or, where there is no previous amplification step, of the preceding step and having a substantially different sequence to said extension nucleic acid sequence; and
    c) an amplification moiety, being limited in all but the final repeat to a nucleic acid sequence; and
  ii) optionally comprising at least one signal moiety being other than a nucleic acid sequence.

b) a single stranded second amplification template comprising:
  i) arranged in a 5' to 3' direction'
    a) an extension nucleic acid sequence comprising said hybridisation nucleic acid sequence of said first amplification template;
    b) a hybridisation nucleic acid sequence comprising the extension nucleic acid sequence of said first amplification template; and
    c) an amplification moiety, being limited in all but the final amplification step to a nucleic acid sequence; and
  ii) optionally comprising at least one signal moiety being other than a nucleic acid sequence;

c) a polymerising agent capable of extending the 3' terminus of the amplification nucleic acid sequence of the previous amplification step or, where there is no previous amplification step, of the preceding step by synthesising a complementary strand to said extension nucleic acid sequence of said first and second amplification templates;

d) a separating agent capable of removing sufficient of said extension nucleic acid sequence of said first and second amplification templates when hybridised to said complementary strand to allow subsequent hybridisation of said hybridisation nucleic acid sequence of said first and second amplification templates to said complementary strand; and e) the reagents and conditions necessary to effect the action of said polymerising agent and separating agent to allow the extension of the 3' terminus of the amplification nucleic acid sequence of the previous amplification step or, where there is no previous amplification step, of the preceding step by the synthesis of a plurality of sequences complementary to said extension nucleic acid sequences of said first and second amplification templates;

iii) detecting any bound first and/or second amplification template from the amplification step or steps; and iv) correlating the results of detection step (iii) with the presence of said target molecule.

The removal of said extension nucleic acid sequence of said first and second amplification templates may be achieved by the use of a 5' double-stranded exonuclease against whose activity said hybridisation nucleic acid sequence of said first amplification template and said hybridisation nucleic acid sequence of said second amplification template are protected.

Locator Probe.

The locator probe contains two distinct regions, the target binding moiety and the amplification nucleic acid sequence. The function of the target binding moiety is to locate to and interact with the target molecule so as to become located at that point. The target binding moiety may comprise anything capable of specifically binding the target molecule. For example in the case of the target molecule being a nucleic acid sequence, the binding moiety may comprise a nucleic acid sequence complementary to the target nucleic acid sequence. Alternatively, it may comprise RNA, a mixture of RNA and DNA or for example PNA. Alternatively, the binding moiety may comprise an antibody or an antigen binding fragment thereof specific to the target molecule (Harlow, E. and Lane, D., "Using Antibodies: A Laboratory Manual", Cold Spring Harbor Laboratory Press, New York, 1998). Other binding mechanisms (for example involving covalent bonding) and reagents will be readily apparent to one skilled in the art. The amplification nucleic acid sequence comprises a nucleic acid sequence that is non-complementary to the target and should not bind to it, therefore rendering it accessible for later binding events. Where the target molecule is a nucleic acid sequence, the Locator probe may be constructed such that its target binding moiety and amplification nucleic acid sequence are oligonucleotides joined using a 5'-3' linkage, or alternatively using a 5'-5' linkage such that each region possessed an extendible free 3' end. Where the target binding moiety is an antibody or antigen binding fragment, the signal nucleic acid moiety may be covalently bound to it using methods known in the art (see, for example, Ito, W. and Kurosawa, Y., 1993, Journal of Biological Chemistry, 268(27): 20668–20675).

Primary Amplification Template and the Primary Structure.

The amplification template is designed to hybridize via its hybridisation region (its hybridisation nucleic acid sequence) to a complementary nucleic acid sequence. Under the appropriate reaction conditions the 3' end of this hybridized complement can be extended to create a complement to the extension region (the extension nucleic acid sequence) of the amplification template. Selective removal of the extension region of the amplification template then leaves a newly synthesized single stranded region to which an additional amplification template can hybridize. A repetition of the steps of hybridisation, extension and removal results in an extended structure composed of multiple repeats of the amplification template. To distinguish this structure from others which may be subsequently generated it is referred to as the Primary Structure. The amplification templates involved in its construction are referred to as primary amplification templates.

Within the Primary Structure are the amplification moieties of the incorporated primary amplification templates. These regions, being non-complementary to the target or Primary Structure, are available to be hybridized with appropriately labeled Detection probes.

If the hybridisation region of the primary amplification template is designed for example to be complementary to the amplification nucleic acid sequence of the Locator probe, then the Primary Structure would be attached to the Locator probe which itself would be attached to the target. Hybridisation of the Detection probes to the Primary Structure would therefore provide a linearly amplified number of signal generating sites linked to the target sequence.

Secondary Amplification Templates and the Secondary Structure.

As an alternative to providing hybridisation nucleic acid sequences for subsequent detection by e.g. detection probes, the primary template amplification moieties incorporated into the Primary Structure can act as complements to the hybridisation region of secondary amplification templates.

The hybridisation region (i.e. the second amplification template hybridisation nucleic acid sequence) is designed to be complementary to the amplification moiety of the primary amplification template. Under the appropriate reaction conditions the 3' end of the primary template amplification moiety can be extended to create a complement to the extension region of the secondary amplification template. Selective removal of the extension region of the secondary template then leaves a newly synthesized single stranded region to which an additional secondary amplification template can hybridize. A repetition of the steps of hybridisation, extension and removal results in multiple extended structures (composed of multiple repeats of the secondary template) attached to the Primary Structure. This structure is referred to as the Secondary Structure.

The incorporated amplification moieties of the secondary templates being non-complementary to the target, Primary Structure or Secondary Structure are available to be hybridized to by appropriately labeled Detection probes. Overall a non-linear increase in the number of target associated signal generating sites is provided by the generation of the Secondary structure.

Each reaction, which results in the assembly of a structure, is referred to as a repeat. The first repeat generates the Primary Structure, the second repeat the Secondary structure and so on. Tertiary and Quaternary structures etc. can be readily generated in this fashion by carrying out the appropriate number of repeats. The number of repeats carried out will depend on the application and will reflect the sensitivity required.

Separating Agents

The generation of the extended Primary or Secondary structure etc., relies on the removal of the extension region of the amplification template once the complement to that region has been made. The "uncovering" of this newly synthesized strand provides a site for another amplification template to hybridize and thus continue the assembly process. Separating agents are responsible for removal of the extension region. These separating agents may include any one or combination of the following: a 5' double strand specific exonuclease (such as T7 gene 6 exonuclease, or Lambda exonuclease); a restriction endonuclease; an RNase (such as RNase H); elevated temperature; or chemical denaturation.

Selective removal of the extension region, whilst ensuring the other regions of the incorporated amplification template remain attached to the growing structure requires some means of controlling or limiting the action of the separating agents. Protection against exonuclease may be achieved through the use of nucleotide analogues or synthetic nucleic acid sequences (e.g., phosphorothioate linkages or 2'-O-Methyl RNA respectively). The inclusion of these synthetic blockers can restrict the activity of the exonucleases to those areas where they are required.

The incorporation of modified linkages can also modify the activities of restriction enzymes, resulting in double stranded cleavage, single stranded nicking or non-restriction of restriction enzyme recognition sites composed of the same base sequence. Deoxynucleotide phosphorothioates, methylated nucleotides and boronated deoxynucleoside triphosphates are all examples of suitable analogues which when incorporated into recognition sites could modify the activities of their restriction enzymes.

The use of chimeric RNA:DNA Amplification templates allows the selective removal of defined portions of the Template using RNase H which acts on the RNA portion of RNA:DNA hybrids.

If in the first and second embodiment the separating agent is a 5' double strand specific exonuclease, the hybridisation region of the amplification templates and the 5' terminus of the Locator probe would be protected by the inclusion of modified linkages or synthetic nucleotide analogues. If the separation agent is RNase H then the extension region of the amplification templates would be composed at least in part of RNA whilst the hybridisation region would be composed of DNA. Where the separating agents have temperature optima of 37° C., they could be used in conjunction with a polymerase such as Klenow (exo-) polymerase. In such a case, the method may operate isothermally at 37° C. Alternatively, the method may of course be performed at more than one temperature.

If the separating agent used is a restriction endonuclease there is the potential to operate the system using a variety of formats, examples and advantages of which are given below:

1. The method may be performed isothermally to provide a rapid qualitative result, or to temperature cycle to provide a less rapid but quantitative result.
2. The method may be operated at temperatures higher than 37° C. to provide temperature controlled stringency, (an important facility given the length and complexity of the Amplification templates used).

3. The activities of restriction endonucleases are defined, well characterized and sequence based, more so than exonucleases such as T7 gene exonuclease and Lambda exonuclease, whose substrate specificity can vary.
4. The combination and concerted action of restriction endonucleases and polymerases under a single set of reaction conditions has been demonstrated frequently.
5. The latitude in operating temperatures allows for a more flexible approach in design rationale, particularly with respect to using different materials such as PNA and 2'-O-Methyl RNA.

In the case of a separating agent being a restriction endonuclease, one or more restriction sites are incorporated in the extension and hybridisation regions of the amplification templates. Those sites in the hybridisation region may be protected by the incorporation of nucleotide analogues at the site of enzymatic cleavage. Those sites in the extension region are unmodified. Hybridisation of the amplification template and creation of a complement to the extension region results in the formation of double stranded recognition sites for the restriction enzymes. Use of one or more modified dNTPs in the reaction mix results in the newly synthesised strand being protected. The enzyme nicks the sites in the extension region of the amplification template and at the operating temperature used, or by elevating the temperature, the resultant fragments are dissociated. This provides a single stranded site to which an additional amplification template can hybridize to continue the assembly process.

Restriction enzyme used as described above must belong to that group which is capable of nicking the unprotected strand of a hemi-modified enzyme recognition site. It is also important that the recognition site sequence is non-palindromic such that amplification templates which self hybridize are not substrates for double stranded cleavage by the restriction enzyme. An example of a suitable enzyme is BsoB1. It is also possible to use enzymes whose activity is naturally restricted to nicking of a single strand as opposed to double stranded cleavage. An example of this kind of enzyme is N.BstNB1 which has the recognition sequence of SEQ ID NO: 1. When such an enzyme is used, it is unnecessary to include dNTP analogues in the reaction mix to protect the newly synthesised strand.

If the method of the present invention is operated isothermally then the reaction is relatively rapid (compared to non-isothermal methods) but qualitative in the signal output generated. Thermocycling (whereby nicked fragments dissociated at a higher temperature than the operating temperature of the restriction enzyme) can be used to generate a signal output that provides quantitative information.

In a third embodiment, the present invention provides a method for detecting a target molecule, utilising a restriction enzyme and polymerase, and comprising the steps of:
 i) contacting a sample with a locator probe comprising a binding moiety specific for said target molecule and an amplification nucleic acid sequence to produce a target molecule-locator probe complex, said amplification nucleic acid sequence having one or more restriction sites for a restriction endonuclease when hybridised to a complementary strand;
 ii) producing an amplification structure bound to any complex produced in the preceding step by performing one or more times the amplification step of treating said sample and locator probe with:
  a) a single stranded amplification template comprising:
   i) arranged in a 5' to 3' direction:
    a) an extension nucleic acid sequence;
    b) a hybridisation nucleic acid sequence complementary to the amplification nucleic acid sequence of the previous amplification step or, where there is no previous amplification step, of the preceding step and having substantially the same sequence as said extension nucleic acid sequence; and
    c) an amplification moiety, being limited in all but the final amplification step to a nucleic acid sequence; and
   ii) optionally comprising at least one signal moiety being other than a nucleic acid sequence;
  b) a polymerising agent capable of extending the 3' terminus of the amplification nucleic acid sequence of the previous amplification step or, where there is no previous amplification step, of the preceding step by synthesising a complementary strand to said extension nucleic acid sequence of said amplification template;
  c) said restriction endonuclease; and
  d) the reagents and conditions necessary to:
   i) effect the action of said polymerising agent and separating agent to allow the extension of the 3' terminus of the amplification nucleic acid sequence of the previous amplification step or, where there is no previous amplification step, of the preceding step by the synthesis of a plurality of sequences complementary to said extension nucleic acid sequence of said amplification template; and
   ii) effect dissociation of nucleic acid strands which have been cut by said restriction endonuclease activity from uncut complementary strands whilst not effecting dissociation of uncut nucleic acid strands from uncut complementary strands;
 iii) detecting any bound amplification template from the amplification step or steps; and
 iv) correlating the results of detection step (iii) with the presence of said target molecule.

In particular, amplification step (ii) may be performed at least twice.

Said amplification nucleic acid sequence and said hybridisation nucleic acid sequence may have nucleotide modifications which prevent cleavage by said restriction endonuclease, and said reagents including at least one modified nucleotide which, when incorporated into said complementary strand by said polymerising agent, prevent cleavage of said complementary strand by said restriction endonuclease.

Said hybridisation nucleic acid sequence may have at least one nucleotide modification which prevents cleavage by said restriction endonuclease, said restriction endonuclease having single stranded nicking activity only.

In the first three embodiments of the present invention, where the amplification moiety is not a nucleic acid sequence (i.e. in the final repeat of the amplification step) it need not be located 3' to the hybridisation nucleic acid sequence. Instead it must be located sufficiently 3' to the extension nucleic acid sequence such that it is not separated from the hybridisation nucleic acid sequence by the separating agent.

For example, the amplification moiety may comprise a biotin molecule (detectable using standard techniques) conjugated to the hybridisation nucleic acid sequence, probably (but not necessarily) at its 3' end.

Alternatively, the amplification moiety may comprise a fluorophore. For example, a fluorophore/quencher technique (such as that of Molecular Beacons) may be employed (as used in, for example, fluorescent PCR). A quencher moiety may be conjugated to the 3' region of the extension nucleic acid sequence, and a fluorophore moiety conjugated to the 5' region of the hybridisation nucleic acid sequence, such that when the extension nucleic acid sequence forms part of the amplification template fluorescence is quenched, and when the separating agent has caused the separation of the hybridisation and extension nucleic acid sequences, fluorescence occurs.

Similarly, the signal moieties of the present invention allow for the production of a signal as amplification structures are generated. It may be that it is only desirable to detect the production of the amplification structure when amplification is complete, in which case detection may be achieved without using any signal moieties. Alternatively, it may for example be desirable to have real-time signal generation as amplification proceeds, in which case a signal moiety such as a fluorophore/quencher combination located on the hybridisation and extension nucleic acid sequences as described above may be employed. This will allow for the generation of a detectable fluorescent signal as the separating agent removes the extension nucleic acid sequence from amplification templates.

Amplification templates may consist of fewer than the three regions. A fourth embodiment of the present invention uses amplification templates that comprise in the 5-3' direction an extension nucleic acid region and a hybridisation nucleic acid region. The 3' terminus of the amplification template is modified to prevent extension.

The steps of hybridisation, extension and separation can be applied as with the first and second embodiments to generate a Primary Structure. If the amplification templates do not contain modified linkages to protect the hybridisation region, then exonuclease digestion can continue until the amplification template is completely removed. The resultant structure will then consist of a single stranded extended Locator probe amplification moiety attached via the Locator probe binding moiety to the target sequence. This can be detected using a complementary labelled detection probe. If generation of a Secondary Structure rather than detection is required, the structure is instead contacted with an additional secondary probe comprising in the 5'-3' direction a hybridisation nucleic acid region and an amplification moiety. Any of this probe which remains unhybridized can be removed by washing prior to addition of secondary amplification templates and generation of the Secondary Structure.

As with the first embodiment, a single amplification template whose extension and hybridisation region sequences are substantially the same can be used, or as with the second embodiment two amplification templates whose extension and hybridisation region sequences are substantially different can be employed.

The Primary structure can also be generated using amplification templates composed of two regions (hybridisation and extension) and a restriction enzyme (as with the third embodiment). The resultant structure will consist of multiple repeats of the amplification template hybridisation region hybridised to the extended amplification moiety of the Locator probe. It will contain no amplification template amplification moieties.

In a fourth embodiment, the present invention provides a method for detecting a target molecule comprising the steps of:
i) contacting a sample with a locator probe comprising:
   a) a binding moiety specific for said target molecule;
   b) an amplification nucleic acid sequence to produce a target molecule-locator probe complex; and
   c) optionally comprising a signal moiety being other than a nucleic acid sequence;
ii) producing an amplification structure bound to any complex produced in the preceding step by performing one or more times the amplification step of treating said complex with:
   a) a single stranded amplification template comprising:
     i) arranged in a 5' to 3' direction:
       a) an extension nucleic acid sequence; and
       b) a hybridisation nucleic acid sequence complementary to the amplification nucleic acid sequence of the previous amplification step or, where there is no previous amplification step, of the preceding step and having substantially the same sequence as said extension nucleic acid sequence; and
     ii) optionally comprising at least one signal moiety being other than a nucleic acid sequence;
   b) a polymerising agent capable of extending the 3' terminus of the amplification nucleic acid sequence of the previous amplification step or, where there is no previous amplification step, of the preceding step by synthesising a complementary strand to said extension nucleic acid sequence of said amplification template;
   c) a separating agent capable of removing sufficient of said extension nucleic acid sequence of said amplification template when hybridised to said complementary strand to allow subsequent hybridisation of said hybridisation nucleic acid sequence of said amplification template to said complementary strand;
   d) the reagents and conditions necessary to effect the action of said polymerising agent and separating agent to allow the extension of the 3' terminus of the amplification nucleic acid sequence of the previous amplification step or, where there is no previous amplification step, of the preceding step by the synthesis of a plurality of sequences complementary to said extension nucleic acid sequence of said amplification template; and
iii) optionally repeating one or more times the steps of treating the products of the previous repeat or, where there is no previous repeat, the products of step (ii) with:
   a) a separating agent capable of removing the remainder of said hybridisation nucleic acid sequence of said amplification template of the previous repeat or step (ii) when hybridised to said complementary strand;
   b) an additional locator probe comprising:
     i) a hybridisation nucleic acid probe specific to said complementary strand of the previous repeat or step (ii);
     ii) an amplification moiety, being limited in all but the final repeat to a nucleic acid sequence; and
   to produce a complex; and
   c) performing step (ii) as defined above, optionally using an amplification template different to that which was previously used;
iv) detecting any bound additional locator probes or amplification template from the amplification step or steps; and
v) correlating the results of detection step (iv) with the presence of said target molecule.

It is also possible to carry out the amplification process using amplification templates comprising in a 5'-3' direction a hybridisation and extension region, and whose sequences differ from each other. In a fifth embodiment, the present invention provides a method for detecting a target molecule, utilising amplification templates whose hybridisation and extension sequences differ, and comprising the steps of:

i) contacting a sample with a locator probe comprising a binding moiety specific for said target molecule and an amplification nucleic acid sequence to produce a target molecule-locator probe complex;

ii) producing an amplification structure bound to any complex produced in the preceding step by performing one or more times the amplification step of treating said complex with:

a) a single stranded first amplification template comprising:
        i) arranged in a 5' to 3' direction:
            a) an extension nucleic acid sequence; and
            b) a hybridisation nucleic acid sequence complementary to the amplification nucleic acid sequence of the previous amplification step or, where there is no previous amplification step, of the preceding step and having substantially the same sequence as said extension nucleic acid sequence; and
        ii) optionally comprising at least one signal moiety being other than a nucleic acid sequence;

b) a single stranded second amplification template comprising:
        i) arranged in a 5' to 3' direction:
            a) an extension nucleic acid sequence comprising said first amplification template hybridisation nucleic acid sequence; and
            b) a hybridisation nucleic acid sequence comprising said first amplification template extension nucleic acid sequence; and
        ii) optionally comprising at least one signal moiety being other than a nucleic acid sequence;

c) a polymerising agent capable of extending the 3' terminus of the amplification nucleic acid sequence of the previous amplification step or, where there is no previous amplification step, of the preceding step by synthesising a complementary strand to said extension nucleic acid sequence of said amplification template;

d) a separating agent capable of removing sufficient of said extension nucleic aid sequence of said first and second amplification templates when hybridised to said complementary strand to allow subsequent hybridisation of said hybridisation nucleic acid sequence of said first and second amplification templates to said complementary strand;

e) the reagents and conditions necessary to effect the action of said polymerising agent and separating agent to allow the extension of the 3' terminus of the amplification nucleic acid sequence of the previous amplification step or, where there is no previous amplification step, of the preceding step by the synthesis of a plurality of sequences complementary to said extension nucleic acid sequence of said amplification template;

iii) optionally repeating one or more times the steps of treating the products of the previous repeat or, where there is no previous repeat, the products of step (ii) with:

a) a separating agent capable of removing the remainder of said hybridisation nucleic acid sequences of said first and second amplification templates of the previous repeat or step (ii) when hybridised to said complementary strand;

b) an additional locator probe comprising:
        i) a hybridisation nucleic acid probe specific to said complementary strand of the previous repeat or step (ii); and
        ii) an amplification moiety, being limited in all but the final repeat to a nucleic acid sequence;
    to produce a complex; and c) performing step (ii) as defined above, optionally using an amplification template different to that which was previously used;

iv) detecting any bound additional locator probes or amplification template from the amplification step or steps; and v) correlating the results of detection step (iv) with the presence of said target molecule.

Hybridisation nucleic acid sequences of the amplification templates of the fourth and fifth embodiments may be modified such that they cannot be extended in a 3' direction by the polymerizing agent.

The removal of said primary amplification template may be achieved by the use of a 5' double strand specific exonuclease.

With the methods of the fourth and fifth embodiments, the removal of said primary amplification template may be achieved through the use of elevated temperature. In such a case, said locator probe may be covalently attached to said target molecule prior to the removal of said primary amplification template. In particular, covalent attachment may be achieved prior to hybridisation of amplification templates.

Prior to the detection step of the first, second and third embodiments a method of steps (i) to (iii) of the fourth or fifth embodiments of the invention may be performed (at least so far as an amplification structure is generated), and vice versa with steps (i) and (ii) of the first, second and third embodiments. Where the amplification moiety in a final amplification step is a nucleic acid sequence then step (i) of the subsequent method may be omitted.

Thus in such a method for detecting a target molecule according to any one of the first, second and third embodiments, and where said amplification moiety of said amplification template from said final amplification step comprises a nucleic acid sequence, step (ii) of a method according to either one of the fourth or fifth embodiments may be additionally performed.

Similarly, in a method for detecting a target molecule according to any one of the fourth or fifth embodiments, prior to said detection step it may additionally comprise step (ii) of a method according to any one of the first, second or third embodiments.

With the first, second and third embodiments (and methods whose final amplification step or repeat involves such embodiments), the step of detecting any bound amplification template may comprise the steps of:

i) treating said sample, locator probe and amplification template or amplification templates with a detection probe which binds specifically to said amplification moiety of said amplification templates; and ii) detecting any bound detection probe.

With the fourth and fifth embodiments (and methods whose final amplification step or repeat involves such embodiments), the step of detecting any bound additional locator probes may comprise the steps of:

i) treating said sample, locator probe and amplification template with a detection probe which binds specifically to said additional locator probe; and ii) detecting any bound detection probe.

The detection probe may have a label which is detected by any one of the group of luminometry, fluorometry, spectrophotometry, and radiometry. For example, the detection probe may be labelled with any one of the group of FAM (carboxyfluorescein), HEX (hexachlorofluorescein), TET (tetrachlorofluorescein), ROX (carboxy-X-rhodamine), TAMRA (carboxytetramethylrhodamine), JOE (carboxy-4', 5'-dichloro-2',7'-dimethoxyfluorescein), or with biotin.

Alternatively or additionally, the detection step may detect any optional signal moieties used in the method. As discussed above, such moieties may comprise fluorophore/quencher combinations (which when detected will comprise solely the fluorophore moiety) or they may for example comprise biotin molecules. The presence of signal moieties allows for the real-time detection of amplification as the methods of the present invention are performed, particularly when the signal moieties comprise fluorophores.

In the various embodiments of the present invention, the amplification step may be performed two or more times, each amplification step being performed using an amplification template having a different extension nucleic acid sequence, hybridisation nucleic acid sequence and amplification moiety to that of the amplification template used in the previous amplification step.

In the various embodiments of the present invention, the target molecule to be detected may be a nucleic acid sequence, the binding moiety of said locator probe comprising a nucleic acid sequence complementary to said target molecule nucleic acid sequence.

The various embodiments of the present invention may be performed using more than one locator probe, each locator probe having the same amplification nucleic acid sequence.

The various embodiments of the present invention may for example comprise two repeats.

Unreacted reagents used in the methods of the present invention may be removed at the end of step (i), each repeat, or detection step, by washing. The unreacted reagents being selected from the group of locator probe, amplification template, primary amplification template, secondary amplification template and detection probe.

The detection of primary and secondary structures generated using embodiments one to five of the invention can be achieved by several different methods.

For example, suitably labelled detection probes can hybridise to the amplification moieties of the amplification templates used in the final step of the first, second and third embodiments. In the fourth and fifth embodiments detection probes may hybridise amplification nucleic acid sequences of locator probes. This requires the use of a separating agent to remove remaining amplification template hybridisation regions, and for a detection probe to then be used which binds to the extended amplification moiety of the locator probe used in the previous repeat. When separation is achieved by denaturation then this additionally requires the use of covalent crosslinking as discussed above (using for example a cross-linking agent such as DZQ (diazirinidylbenzoquinone)).

Alternatively or additionally, the amplification templates may have an internal or 3' terminally located label (i.e. signal moiety) attached that becomes incorporated into the structures as they are generated.

As described above, the amplification templates can be so designed that a fluorophore label in the hybridisation region sequence is separated from a quencher label in the extension region during primary/secondary structure assembly. In this way real time generation of signal is possible.

The invention will be further apparent from the following description, with reference to the several figures of the accompanying drawings, which show, by way of example only, forms of detection of target molecules and signal amplification.

DEFINITIONS

The term "antibody" in its various grammatical forms is used herein to refer to immunoglobulin molecules and immunologically active portions of immunoglobulin molecules, i.e., molecules that contain an antibody combining site or paratope. Such molecules are also referred to as "antigen binding fragments" of immunoglobulin molecules.

Illustrative antibody molecules are intact immunoglobulin molecules, substantially intact immunoglobulin molecules and those portions of an immunoglobulin molecule that contain the paratope, including those portions known in the art as Fab, Fab', F(ab')2 and F(v).

Antibodies and their use are well known in the art, for example as taught by Harlow, E. and Lane, D., "Using Antibodies: A Laboratory Manual", Cold Spring Harbor Laboratory Press, New York, 1998.

As used herein the term "nucleic acid" includes protein nucleic acid (PNA) (i.e. nucleic acids in which the bases are linked by a polypeptide backbone) as well as the naturally occurring nucleic acids (e.g. DNA and RNA), or analogues thereof, having a sugar phosphate backbone.

EXAMPLE 1

Figure 1A:
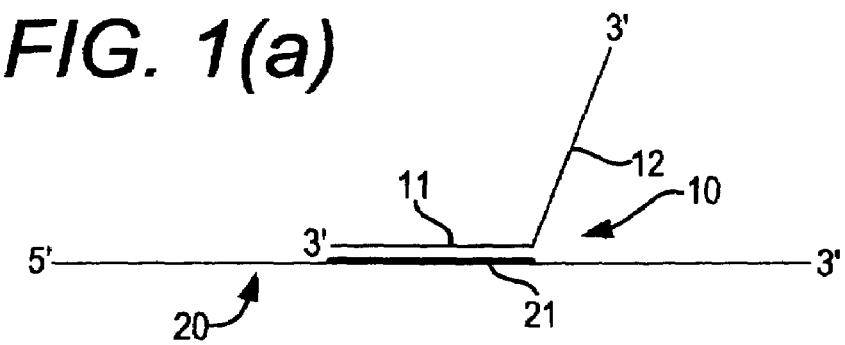
FIG. 1 shows forms of Locator probed hybridised to target nucleic acid sequences.
Figure 1B:
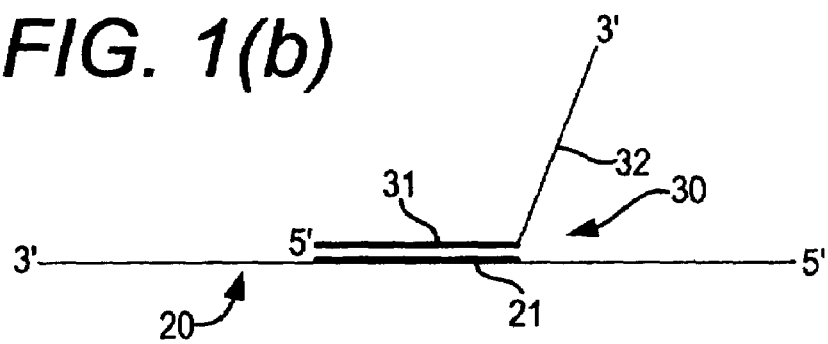

As can be seen from FIG. 1a, Locator probe 10 comprises binding nucleic acid moiety 11 joined by a 5'-5' linkage to amplification moiety 12. Binding nucleic acid moiety 11 hybridises target nucleic acid sequence 21 of target molecule 20. FIG. 1b shows Locator probe 30 comprising binding moiety 31 which is rendered resistant to exonuclease activity by the use of 2'-O-methyl-RNA residues in its synthesis, is joined by a 5'-3' linkage to amplification moiety 32. Binding nucleic acid moiety 31 hybridises target nucleic acid sequence 21 of target molecule 20.

Figure 2:
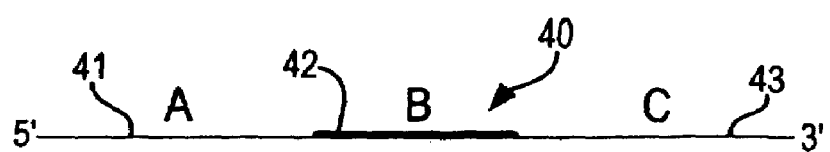
FIG. 2 shows an amplification template used in the first embodiment of the present invention.

FIG. 2 shows primary amplification template 40 comprising arranged in a 5'-3' direction extension region 41, exonuclease-resistant hybridisation region 42 and amplification moiety 43.

Figure 3A:
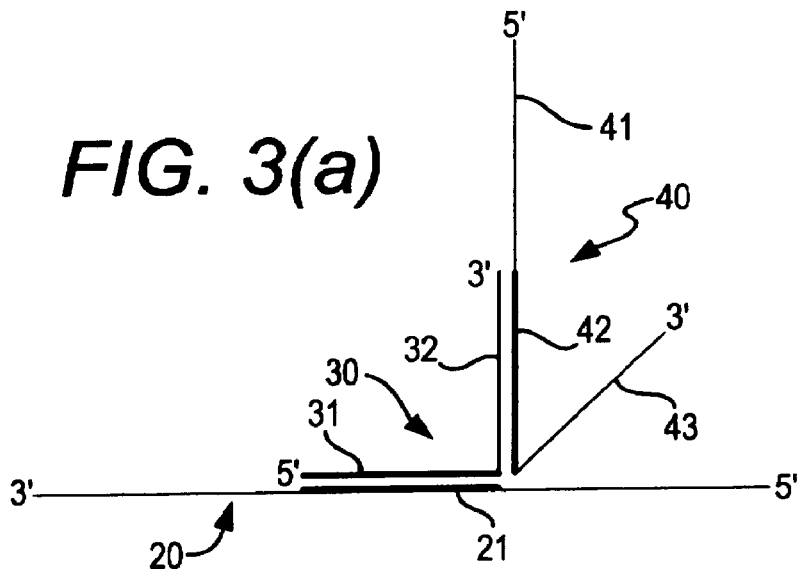
FIG. 3 shows a target molecule detection method according to the first embodiment of the present invention.
Figure 3B:
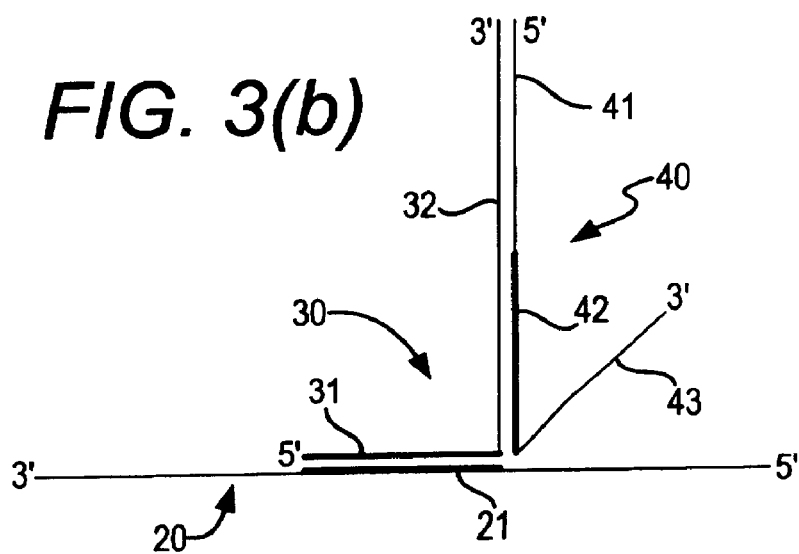
Figure 3C:
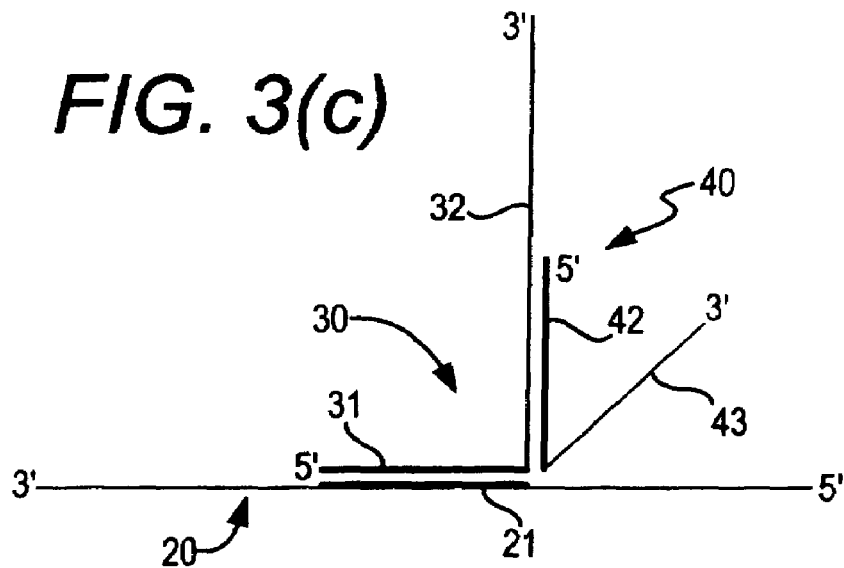
Figure 3D:
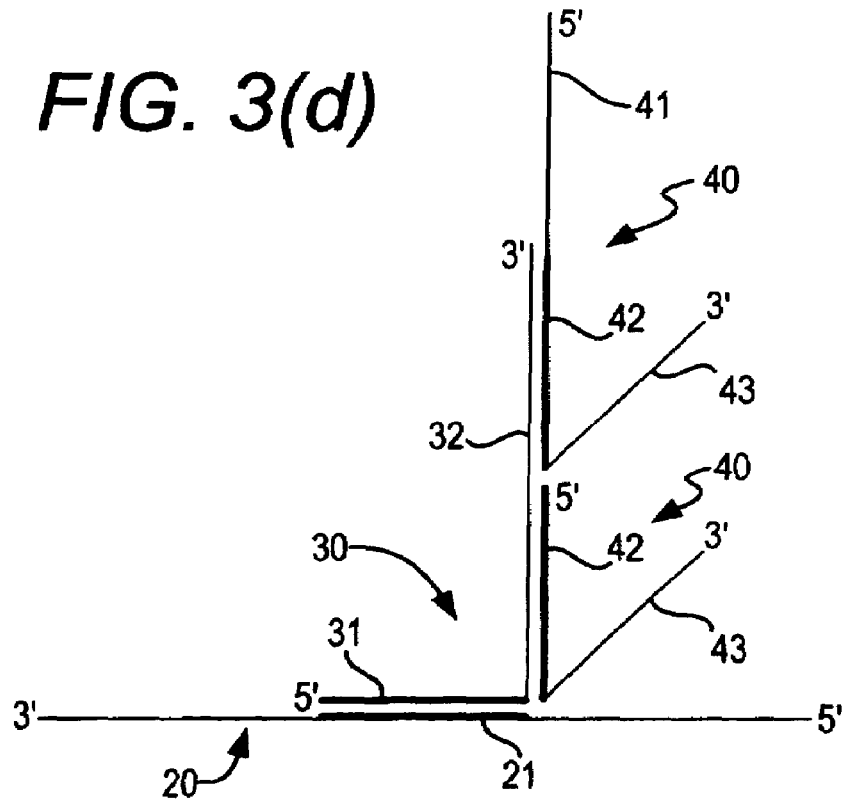
Figure 3E:
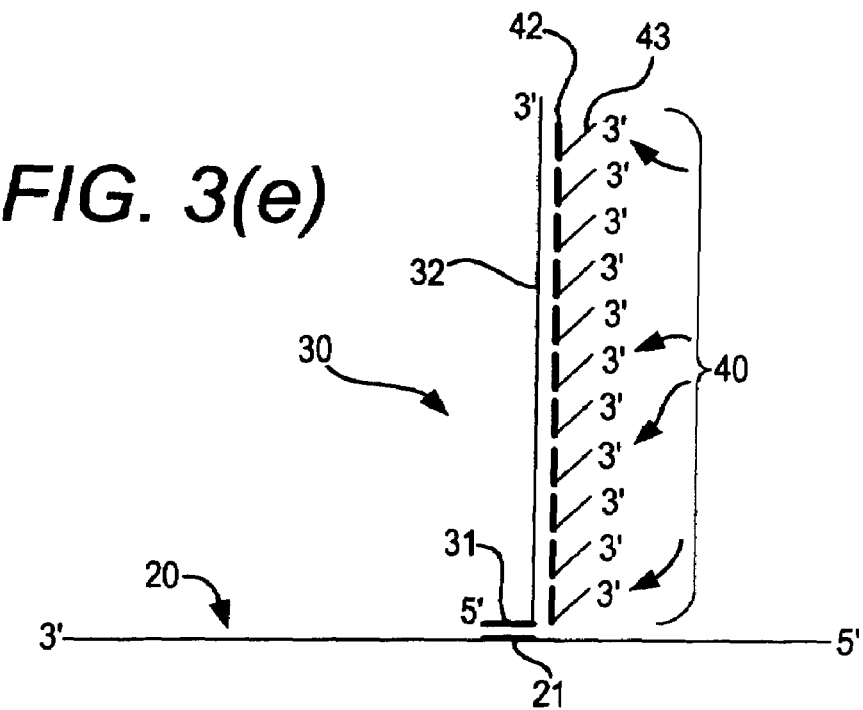

In the method of the first embodiment of the present invention (FIG. 3), hybridisation region 42 of amplification template 40 hybridises to amplification moiety 32 of Locator probe 30 (FIG. 3a). DNA polymerase activity then causes the extension of amplification moiety 32, using extension region 40 as a template strand (FIG. 3b). A 5' double-strand specific exonuclease (not shown) then digests the 5' terminus of the hybridised extension region 41. Exonuclease activity is halted when the enzyme encounters exonuclease resistant hybridisation region 42 (FIG. 3c). Additional amplification template 40 is then able to hybridise to extended nucleic acid signal sequence 32 (FIG. 3d) and the process of extension and exonuclease digestion proceed again to give the arrangement of FIG. 3e.

Figure 3F:
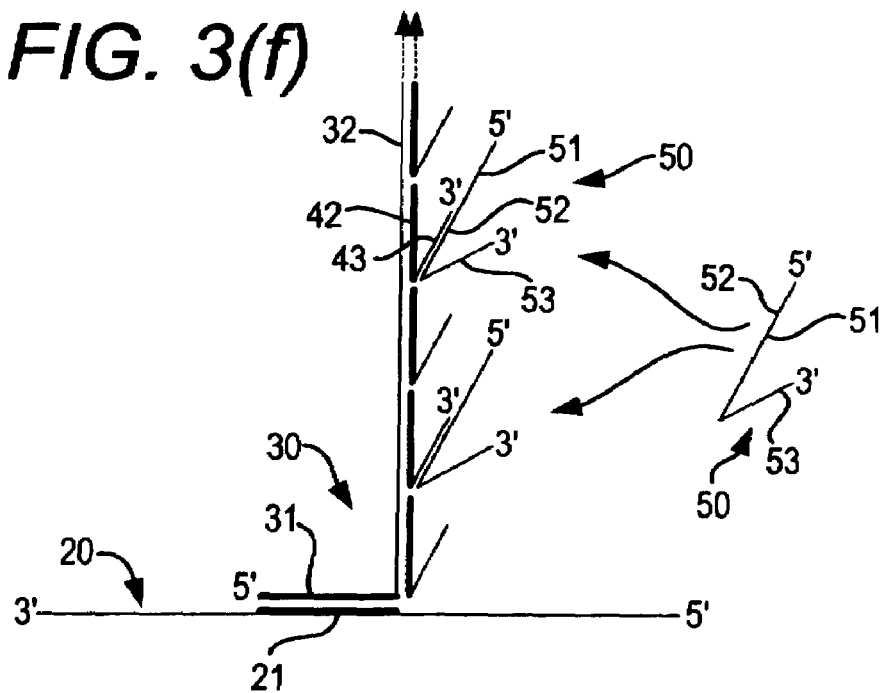
Figure 3G:
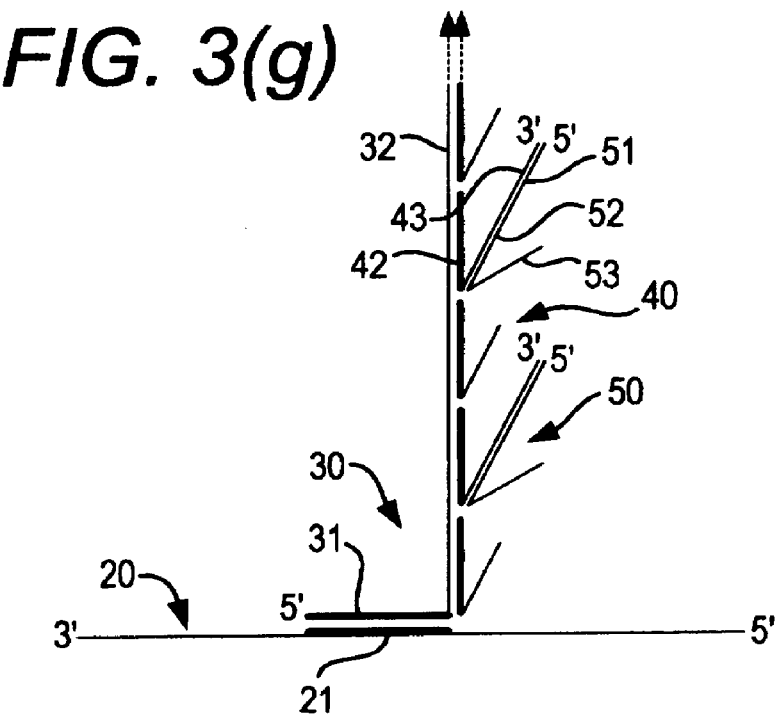
Figure 3H:
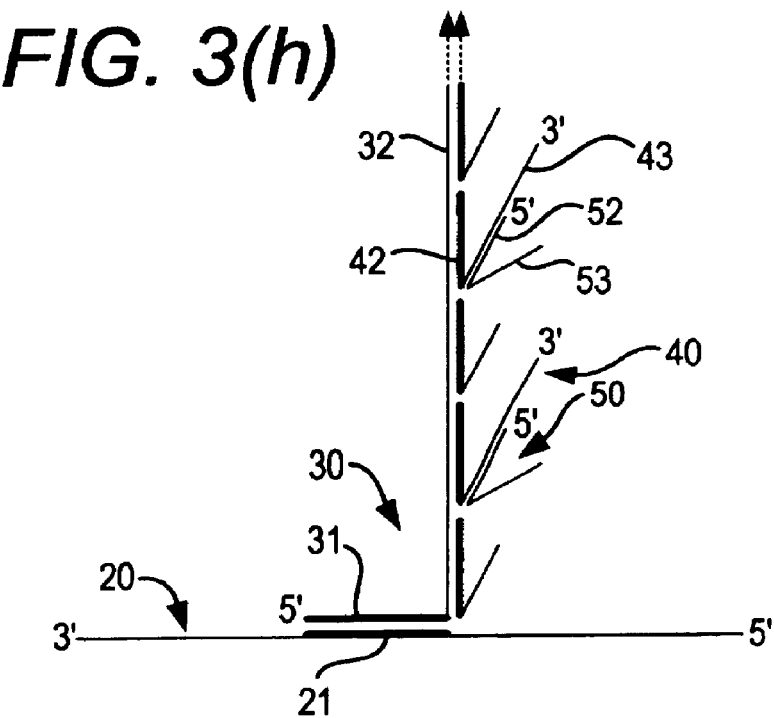
Figure 3I:
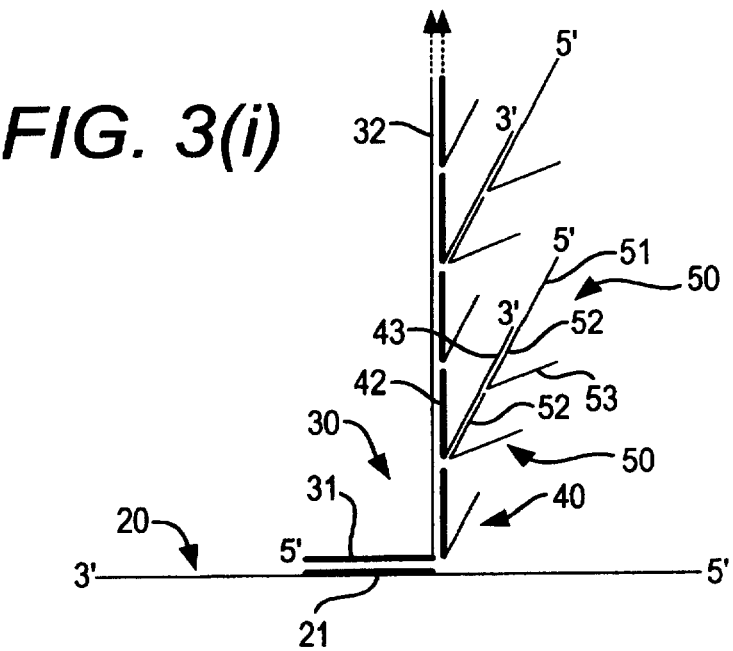
Figure 3J:
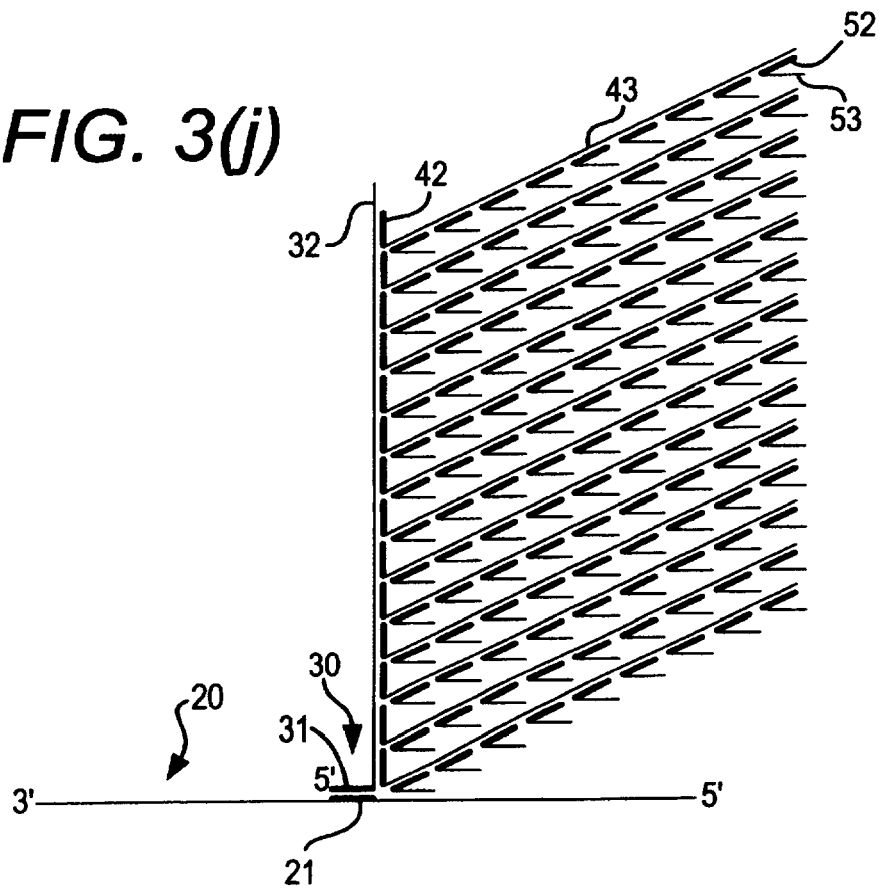
Figure 3K:
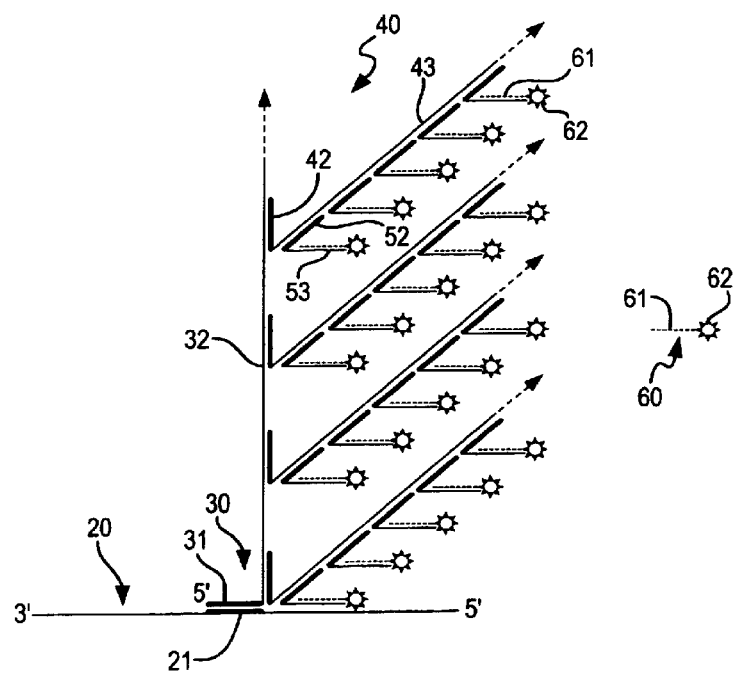

Having washed the reaction mixture to remove unhybridized amplification template 40, the process is then repeated using secondary amplification template 50 comprising extension region 51, hybridisation region 52 and amplification moiety 53 (FIG. 3f). Hybridisation region 52 is complementary to amplification moiety 43. The steps of extension of amplification moiety 43, digestion of extension region 51 and hybridisation of additional amplification template 50 then proceed as above, to create the Secondary Structure. This incorporates large numbers of amplification moiety 53 which are available for hybridisation (FIGS. 3g–3j).

Detection probe 60 comprises signal detection nucleic acid sequence 61 complementary to amplification moiety 53, linked to biotin label molecule 62. After hybridisation of Detection probe 60 and washing to remove any unhybridized probe, biotin label molecules 62 are detected using standard techniques. The result of the detection step is then correlated with the presence of target sequence 21.

Figure 4A:
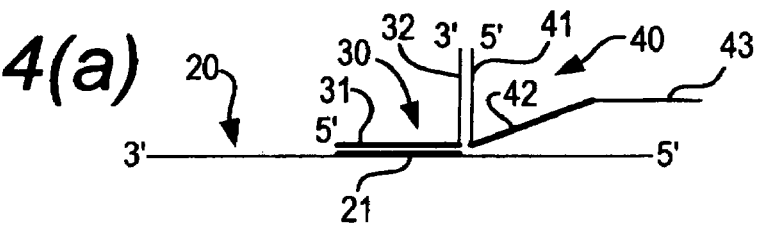
FIG. 4 shows incorrect amplification template binding.
Figure 4B:
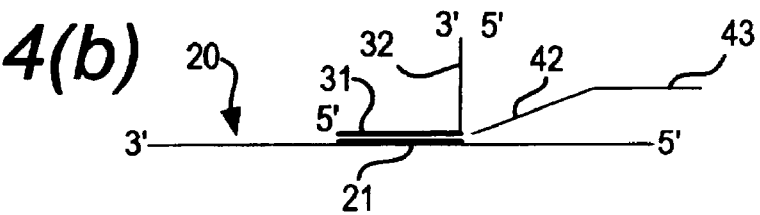
Figure 4C:
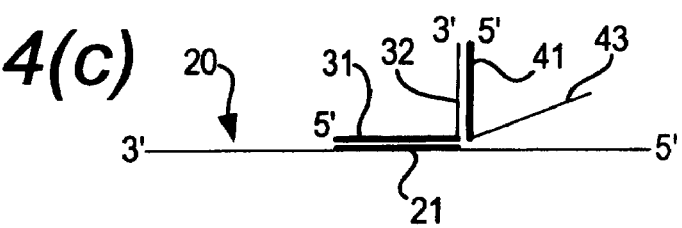

As can be seen from FIG. 4, there are certain undesirable interactions that are possible between for example amplification moiety 32 of Locator probe 30 and extension region 41 of amplification template 40. FIG. 4a shows extension region 41 hybridising to amplification moiety 32. This is then subject to exonuclease activity (FIG. 4b) and, subsequently, hybridisation region 42 of amplification template 40 is able to hybridise to amplification moiety 32. However, since amplification template 40 no longer possesses an extension region 41, it is not possible to extend signal nucleic acid sequence 32 and no further Primary Structure assembly is possible.

EXAMPLE 2

Figure 5:
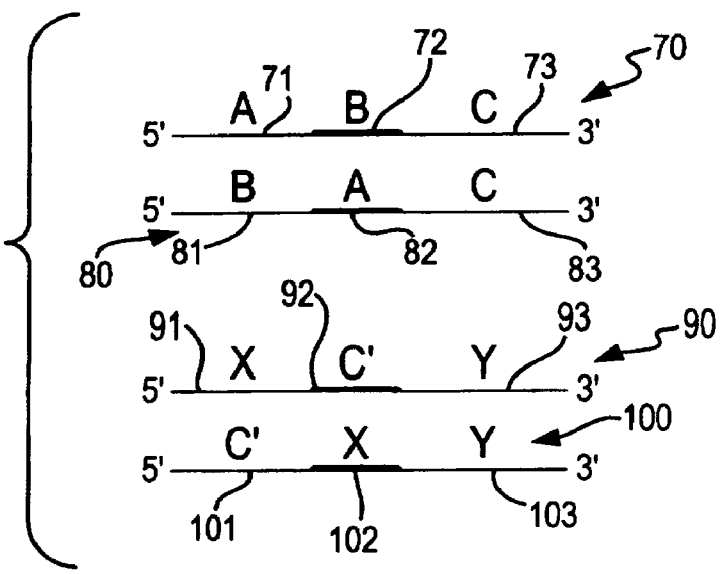
FIG. 5 shows amplification templates used in the second embodiment of the present invention.

FIG. 5 shows pairs of amplification templates used in the method of the second embodiment of the present invention. Primary amplification template 70 comprises arranged in a 5' to 3' direction extension region 71, hybridisation region 72 and amplification moiety 73. Second primary amplification template 80 comprises arranged in a 5' to 3' direction extension region 81 (which has the same sequence as hybridisation region 72), hybridisation region 82 (which has the same sequence as extension region 71) and amplification moiety 73. Extension region 71 and hybridisation region 72 have substantially different sequences, such that they will not hybridise the same nucleic acid sequence. The first secondary amplification template 90 comprises arranged in a 5' to 3' direction extension region 91, hybridisation region 92 (which is complementary to amplification moiety 73 from the previous repeat) and amplification moiety 93. The second secondary amplification template 100 comprises arranged in a 5' to 3' direction extension region 101 (which has the same sequence as hybridisation region 92), hybridisation region 102 (which has the same sequence as extension region 91) and amplification moiety 103. Extension region 91 and hybridisation region 92 have substantially different sequences, such that they will not hybridise the same nucleic acid sequence. Nucleic acid sequences 72, 82, 92 and 102 contain 2'-O-methyl-RNA substituted nucleic acid sequences, ensuring that they are resistant to 5' exonuclease activity.

Figure 6A:
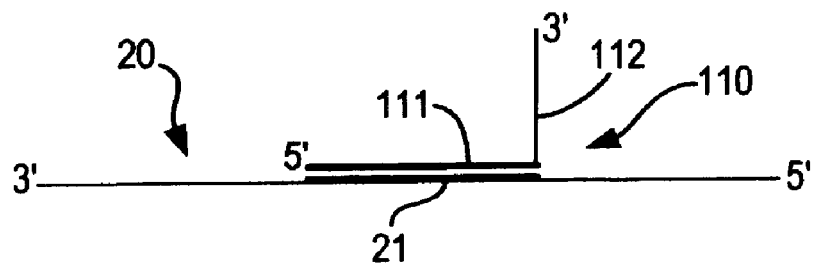
FIG. 6 shows a target molecule detection method according to the second embodiment of the present invention.
Figure 6B:
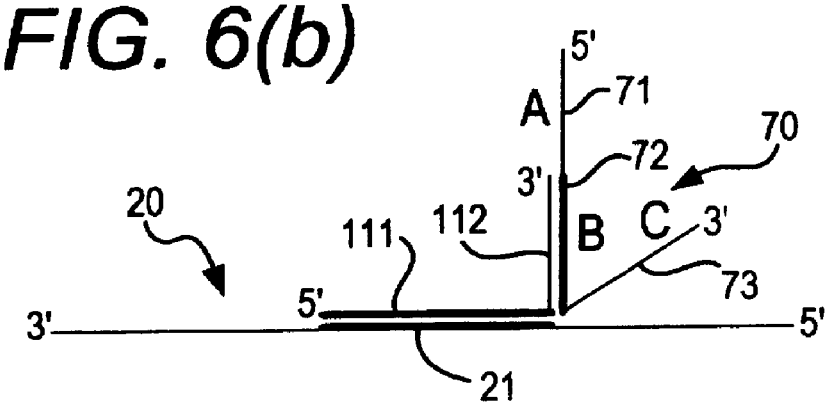

In practice (FIG. 6), target nucleic acid sequence 21 of target molecule 20 is hybridised by binding nucleic acid sequence 111 of Locator probe 110. Binding nucleic acid moiety 111 contains substituted nucleic acids that ensure that it is resistant to 5' exonuclease activity (FIG. 6a). Hybridisation region 72 of first amplification template 70 then hybridises to amplification moiety 112 of Locator probe 110 (FIG. 6b). Since extension region 71 is different to hybridisation region 72 it is unable to hybridise to amplification moiety 112.

Figure 6C:
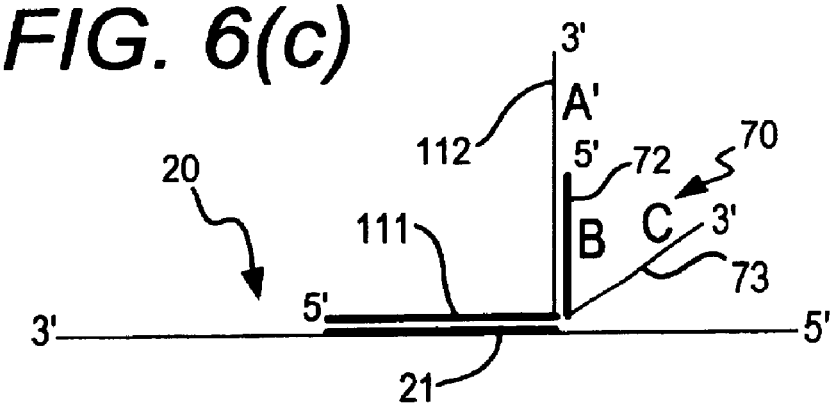

DNA polymerase activity then extends the free 3'-OH end of amplification moiety 112 using extension region 71 as a template. 5' exonuclease activity then digests extension region 71 (FIG. 6c).

Figure 6D:
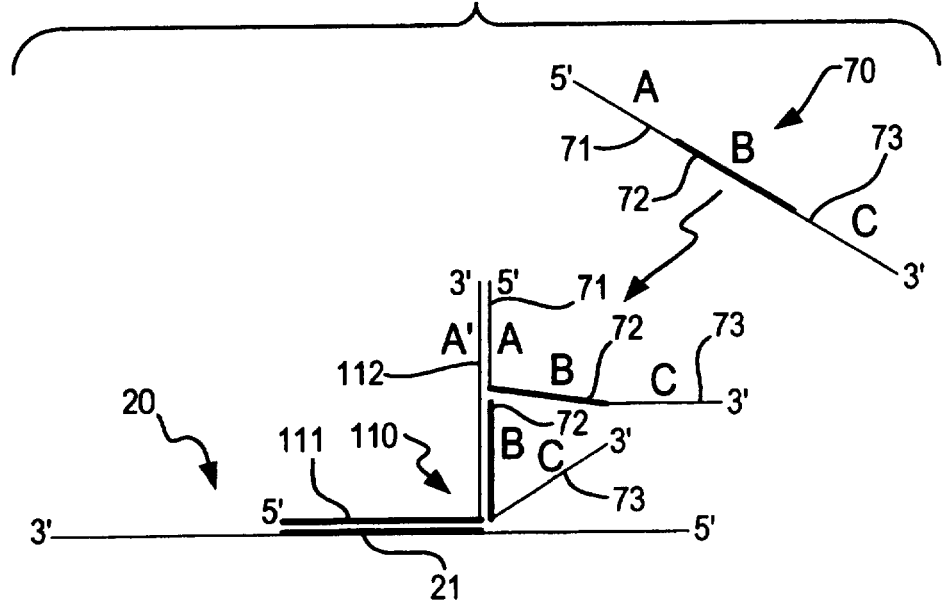
Figure 6E:
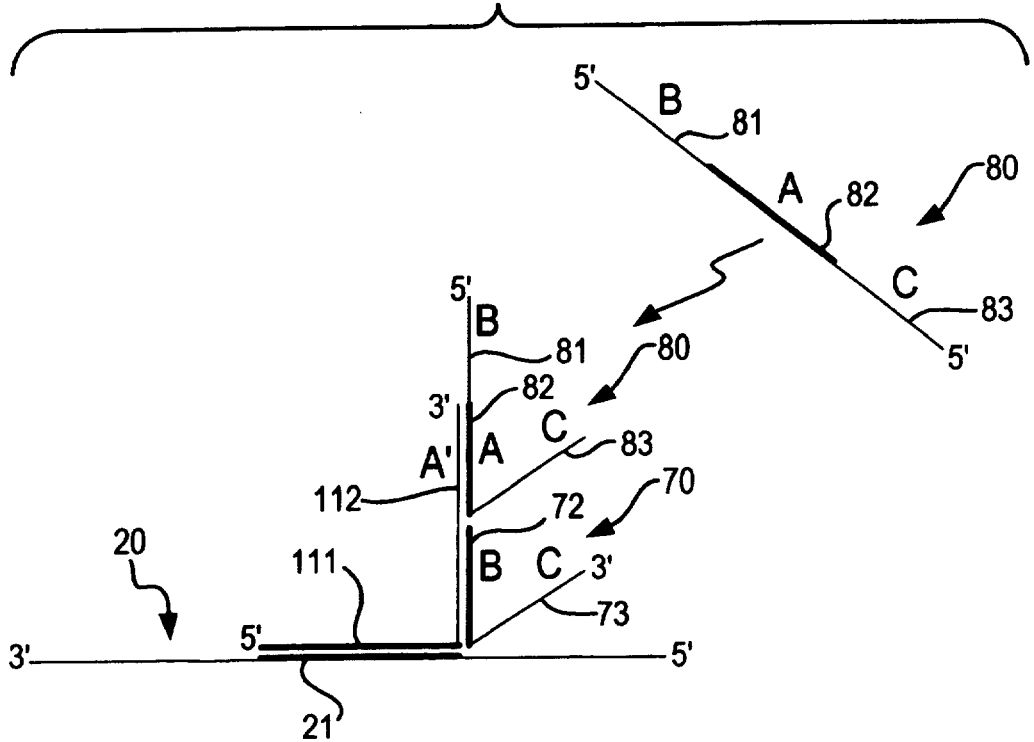
Figure 6:
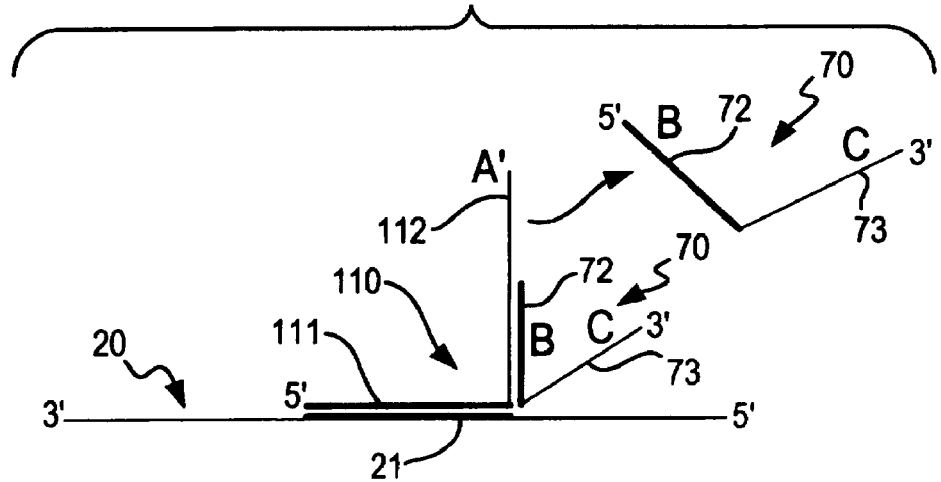
Figure 6:
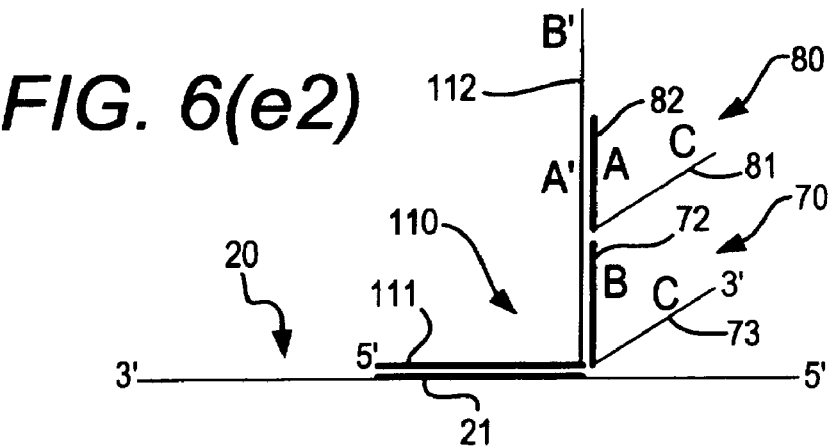

At this point it is possible for extension region 71 of amplification template 70 to hybridise to extended amplification moiety 112 (FIG. 6d, top). However, since extension region 71 is not protected from 5' exonuclease activity, it is digested, leaving extended amplification moiety 112 exposed (FIG. 6e.1). The remains of partially digested amplification template 70 (comprising hybridisation region 72 and amplification moiety 73) are unable to hybridise to extended amplification moiety 112.

Alternatively (FIG. 6d, bottom) hybridisation region 82 of amplification template 80 is able to hybridise to extended amplification moiety 112. Amplification moiety 112 is then further extended by DNA polymerase activity using extension region 81 as a template. Extension region 81 is then digested (FIG. 6e.2) and assembly of the Primary Structure continues, with hybridisation region 72 of amplification template 70 hybridising to the extended amplification moiety 112.

After washing to remove unhybridized amplification templates 70 and 80 Secondary Structure assembly is then performed using amplification templates 90 and 100. The Secondary Structure is then detected and the results of the detection correlated with the presence of the target molecule.

EXAMPLE 3

Figure 7:
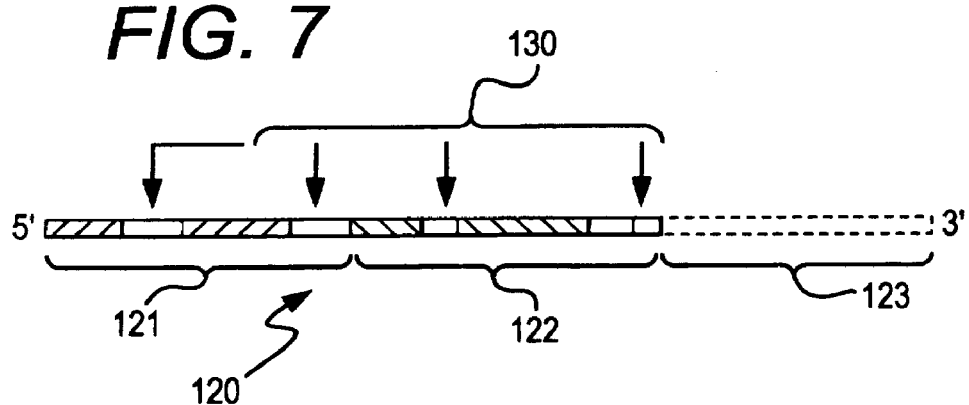
FIG. 7 shows an amplification template used in the method of the third embodiment of the present invention.
Figure 8A:
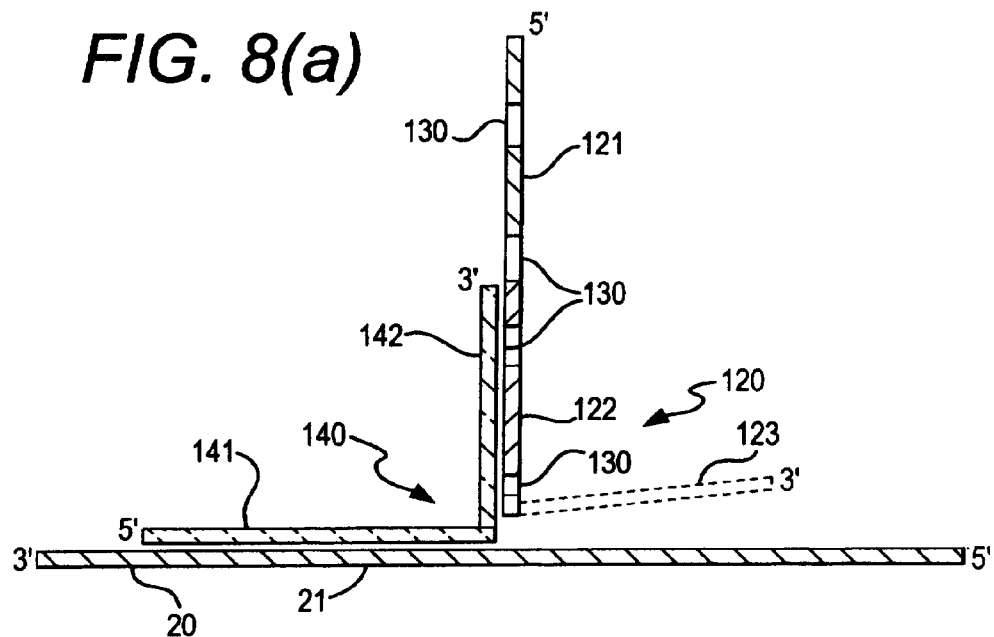
FIG. 8 shows the method of the third embodiment of the present invention.
Figure 8B:
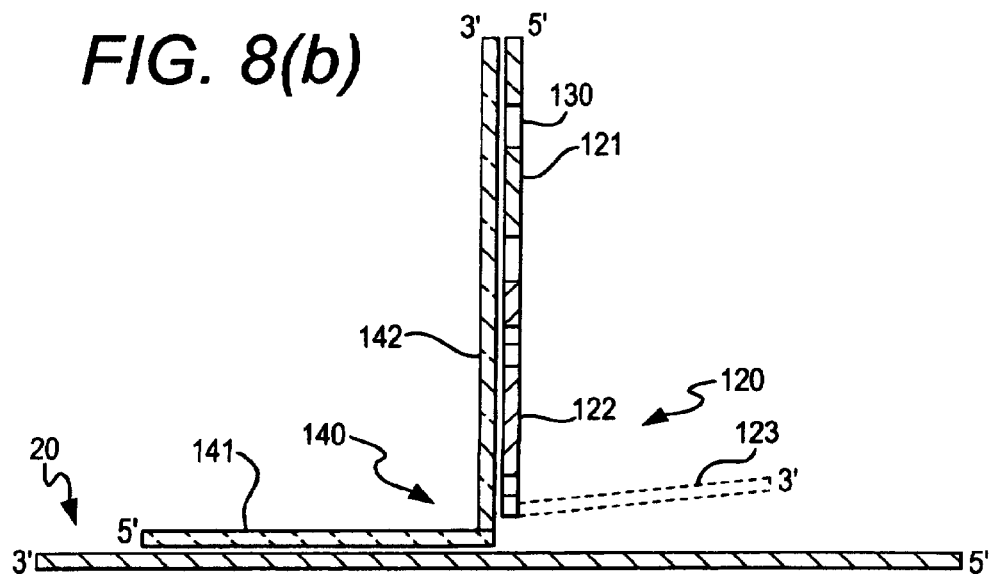
Figure 8C:
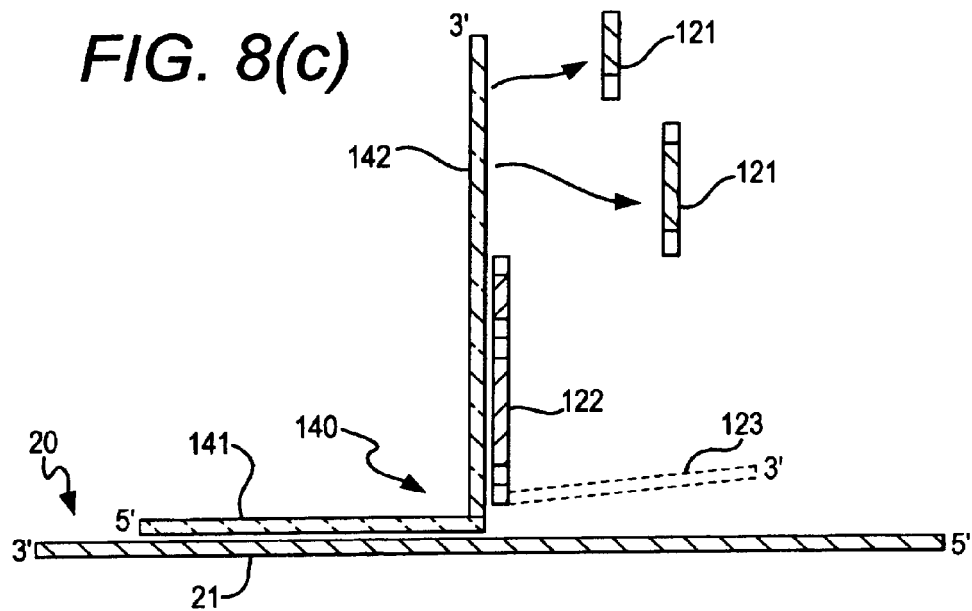
Figure 8D:
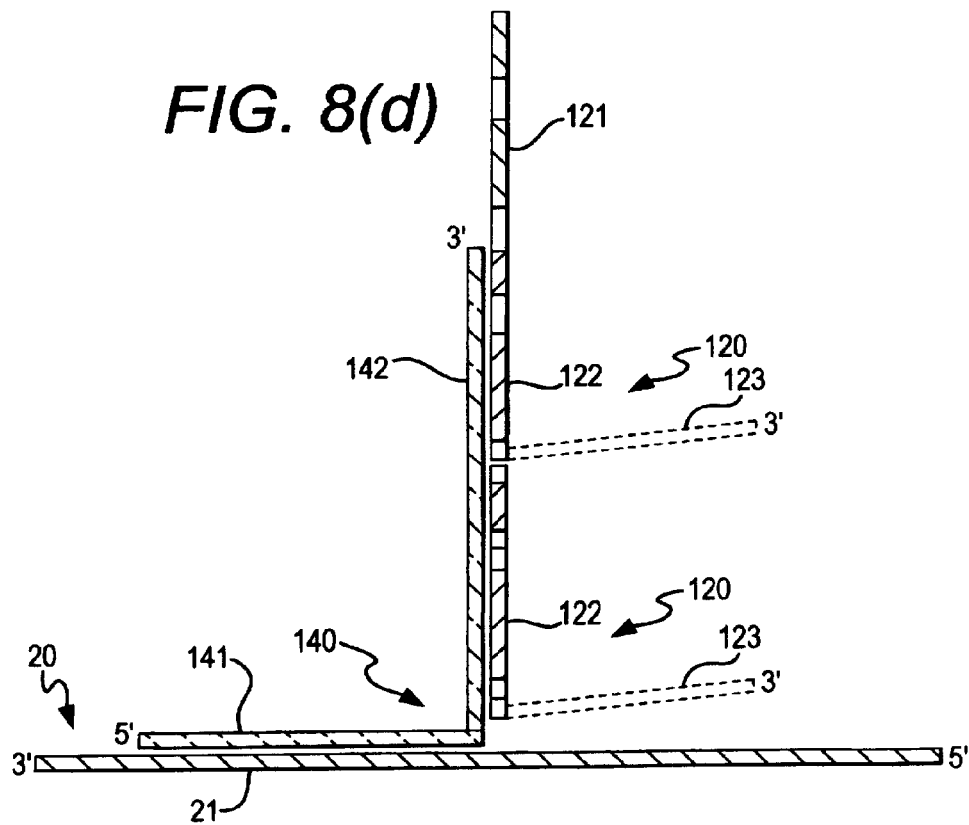

FIG. 7 shows an amplification template used in an embodiment of the third embodiment of the present invention. Amplification template 120 comprises extension region 121, hybridisation region 122 having substantially the same nucleic acid sequence as extension region 121 (at least to the extent that they are both able to hybridise the same nucleic acid sequence), and amplification moiety 123. Extension region 121 and hybridisation region 122 each in this example having two restriction sites 130, the restriction sites of extension region 121 being such that when hybridised to a complementary sequence they are capable of being cleaved by restriction endonuclease activity. However, the restriction sites of hybridisation region 122 have 2'-O-methyl-RNA modified nucleotides such that they are not subject to restriction endonuclease activity.

Signal amplification using the method of the third embodiment of the present invention is achieved as shown in FIG. 8. Binding nucleic acid sequence 141 of Locator probe 140 hybridises to target nucleic acid sequence 21 of target molecule 20. The Locator probe amplification moiety 142 is complementary to hybridisation region 122 of amplification template 120 but has 2'-O-methyl-RNA nucleotide substitutions such that it is not subject to restriction endonuclease activity. Hybridisation region 122 of amplification template 120 then hybridises to amplification moiety 142 (FIG. 8*a*), which is then extended by DNA polymerase activity using extension region 121 as a template (FIG. 8*b*). At least one of the solution phase dNTPs utilised by the polymerase is modified with 2'-O-methyl-RNA substitutions such that its incorporation renders the newly synthesised strand resistant to restriction endonuclease activity.

Restriction endonuclease activity then nicks extension region 121. In an isothermal assay format the resultant fragments is designed so as to dissociate at the operating temperature used. In a thermocycled format the temperature is elevated to allow dissociation of the fragments without concomitant dissociation of uncleaved sequences. Additional amplification template 120 is then able to hybridise to extended amplification moiety 142 and the reaction able to proceed to assemble the Primary Structure. Detection or Secondary Structure assembly is subsequently carried out by repetition of the same basic processes as described above.

EXAMPLE 4

Figure 9A:
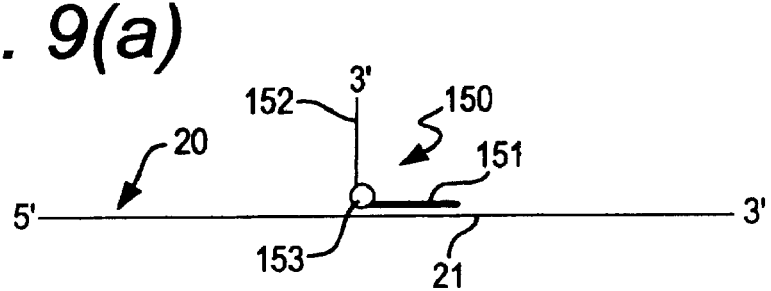
FIG. 9 shows the method of the fourth embodiment of the present invention.

In the fourth embodiment of the present invention (FIG. 9), target nucleic acid sequence 21 of target molecule 20 is hybridised by Binding moiety 151 (which has nucleotide modifications to render it resistant to 5' double stranded exonuclease activity when required) of Locator probe 150 (FIG. 9*a*). Amplification moiety 152 is linked to binding nucleic acid sequence 151 by extension blocker 153 (a 3' propanol addition) such that it has an exposed 3'-OH group. When amplification moiety 152 is acting as the template strand for the synthesis of a complementary strand, the extension blocker prevents the progress of any DNA polymerase beyond the end of the amplification moiety, thereby preventing the displacement of binding moiety 151 from target nucleic acid sequence 21. Once unbound Locator probe has been removed, binding moiety 151 is optionally cross-linked to target sequence 21 prior to Primary Structure assembly.

Figure 9B:
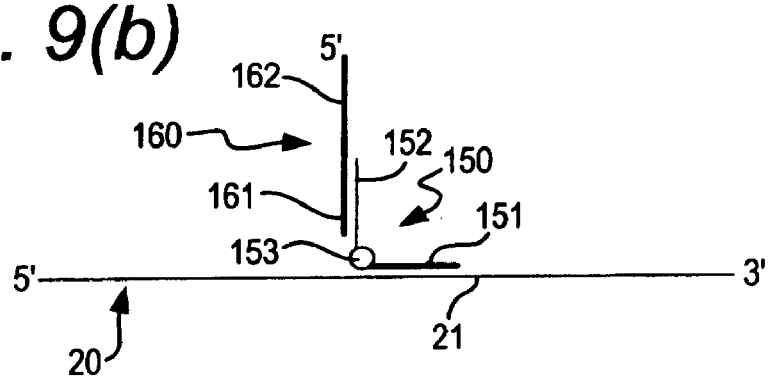
Figure 9C:
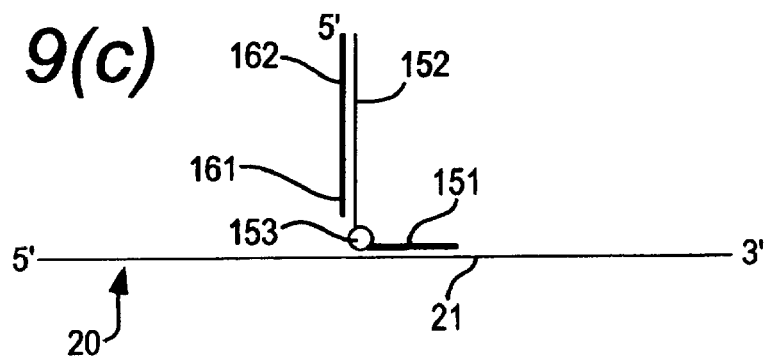
Figure 9D:
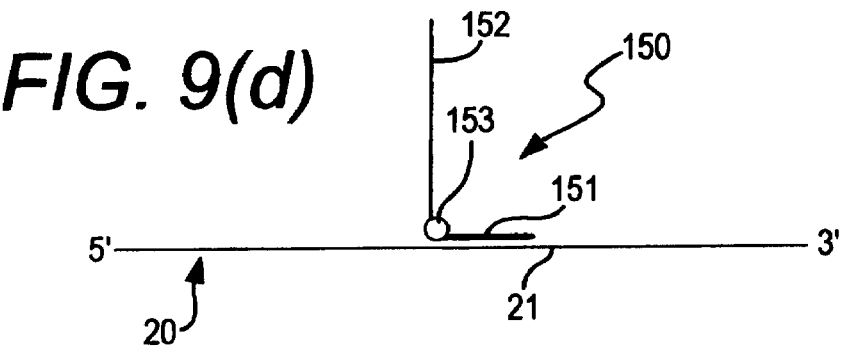
Figure 9E:
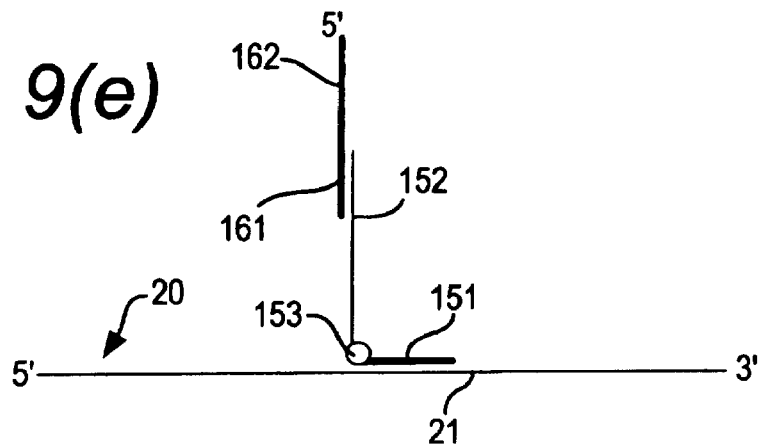

In use, hybridisation region 161 of amplification template 160 hybridises to amplification moiety 152 (FIG. 9*b*). Hybridisation region 161 has an exposed 3'-OH group, as does amplification moiety 152. Extension region 162 then acts as a template strand for the extension of amplification moiety 152, which in turn acts as a template strand for the extension of hybridisation region 161 as far as extension blocker 153 (FIG. 9*c*). 5' double strand exonuclease activity can then digest extended amplification template 160 as shown in this example, leaving free extended amplification moiety 152 (FIG. 9*d*). Alternatively the amplification templates can be completely removed through the use of elevated temperature. Additionally the amplification templates can be designed so as to contain modified and unmodified restriction sites that allow endonuclease cleavage to remove the extension region of the amplification template only.

Figure 9F:
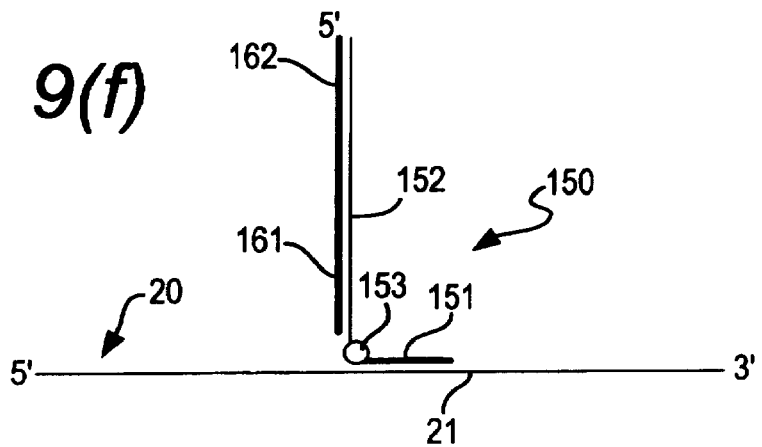
Figure 9G:
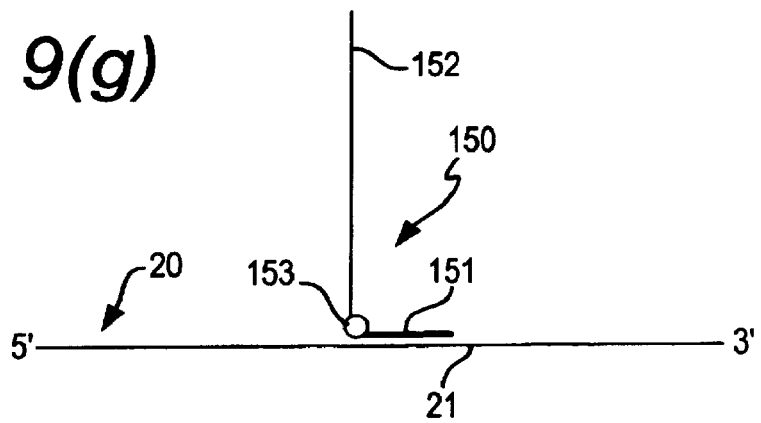
Figure 9H:
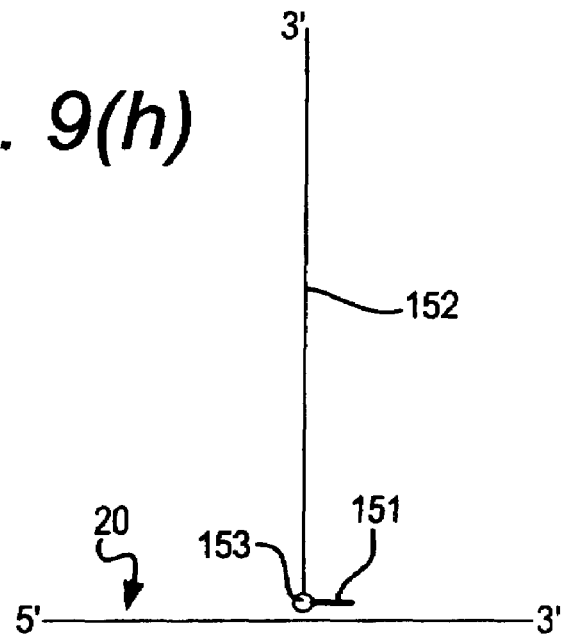

Additional amplification template 160 is then able to hybridise to extended amplification moiety 152 (FIG. 9*e*) and extension region 162 again able to act as template strand for the synthesis of a complementary strand, extending further amplification moiety 152. Similarly, amplification moiety 152 is able act as template strand for the extension of hybridisation region 161 (FIG. 9*f*). Removal of part or all of the extended amplification template 160 is then achieved through 5' exonuclease activity (as in this example), or by elevated temperature, or by a restriction endonuclease (FIG. 9*g*, 9*h*).

Figure 9I:
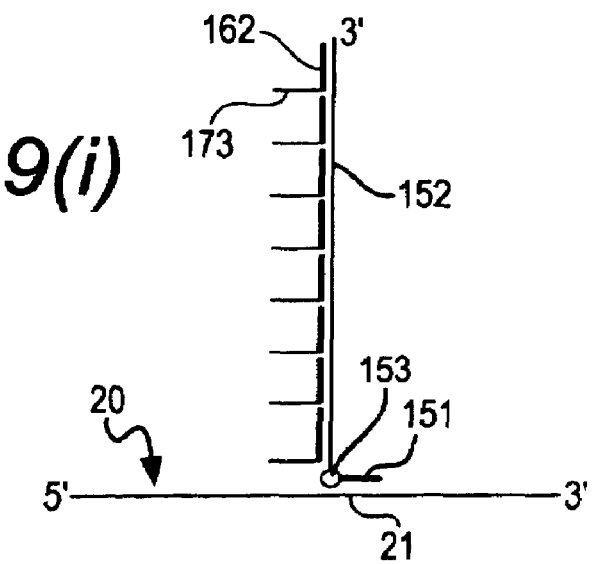
Figure 9J:
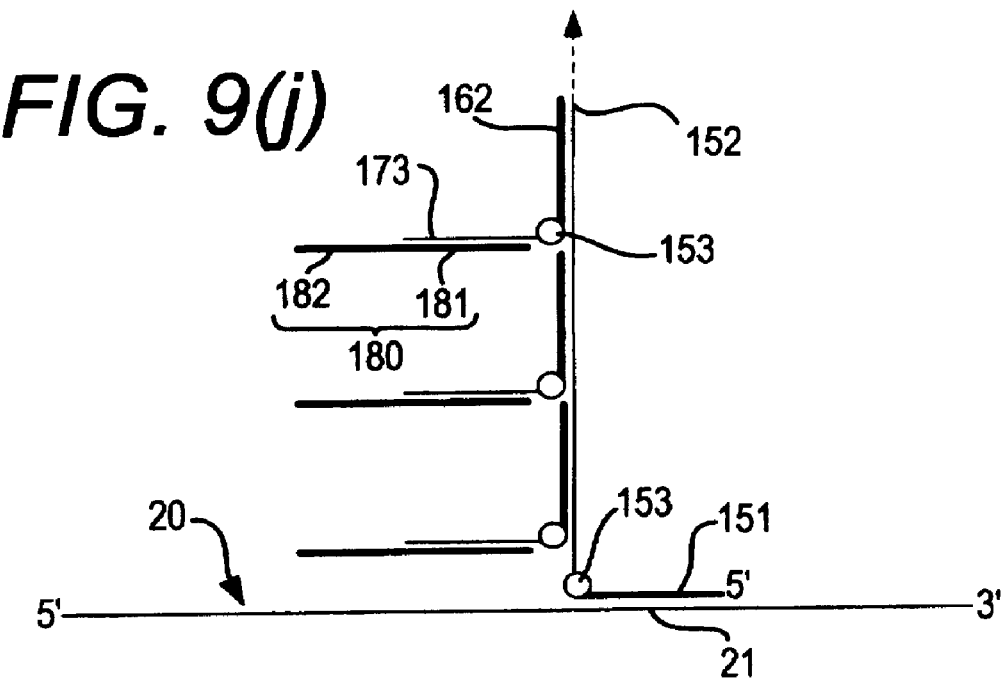
Figure 9K:
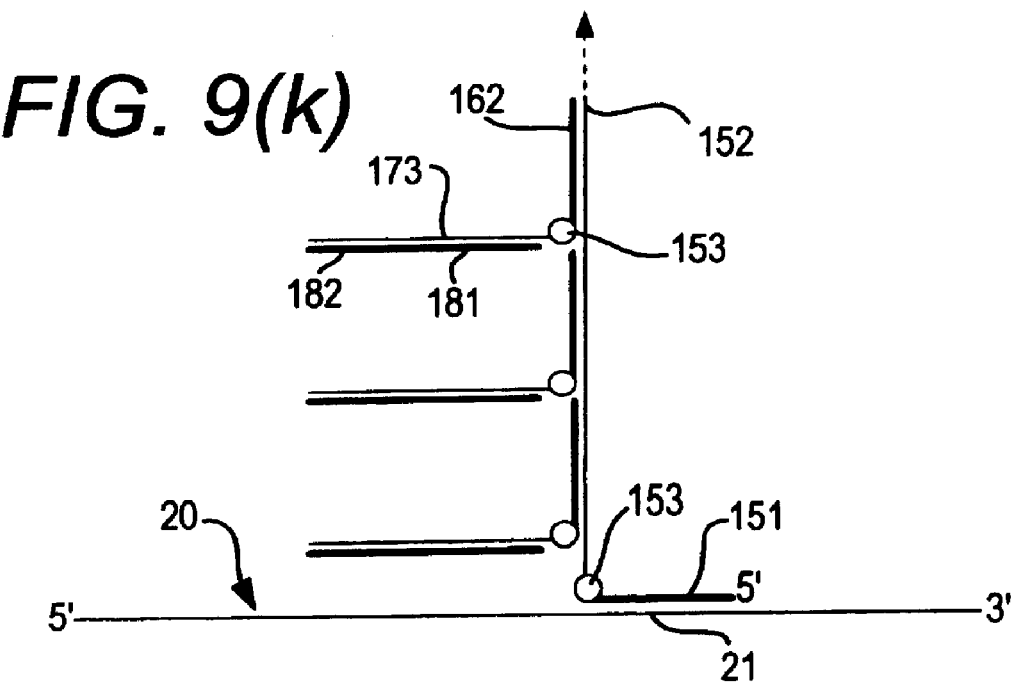
Figure 9L:
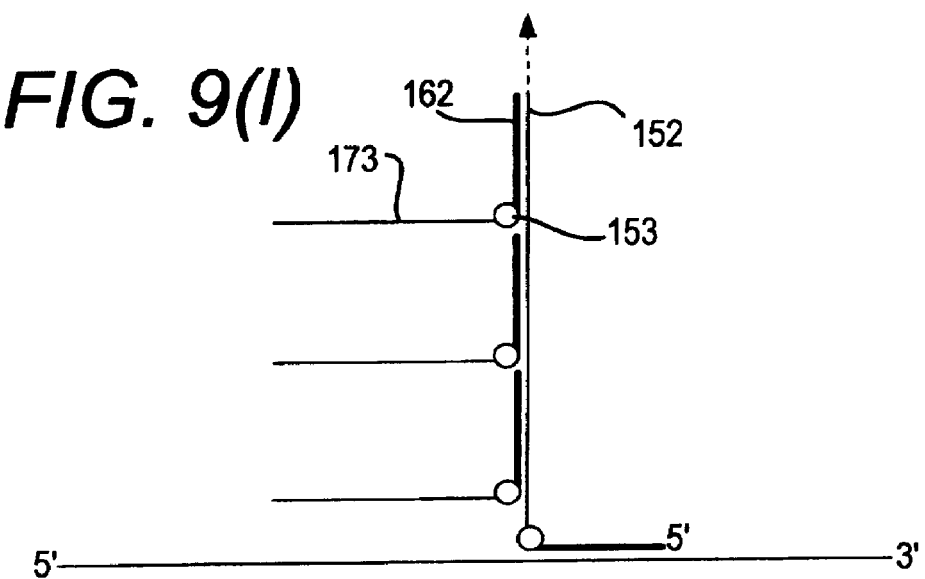
Figure 9M:
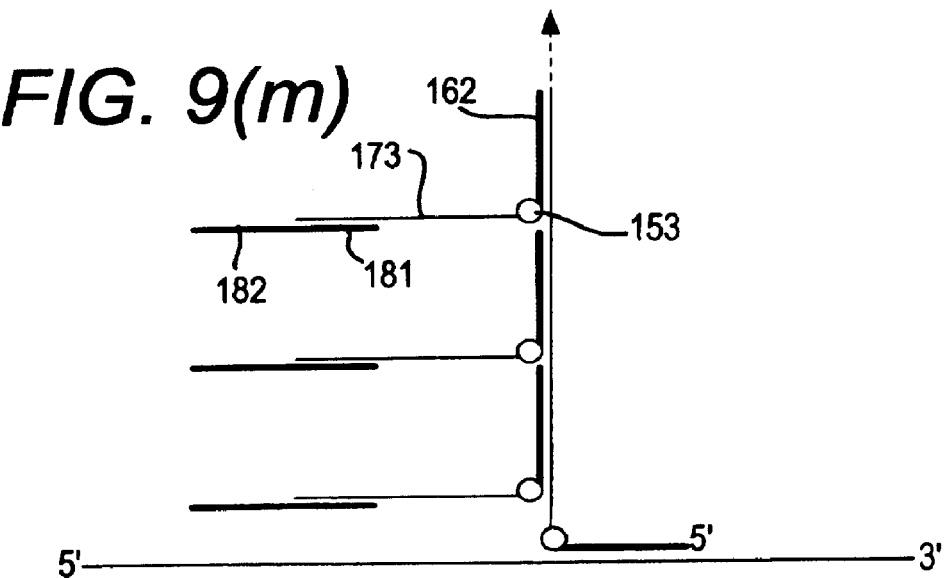
Figure 9P:
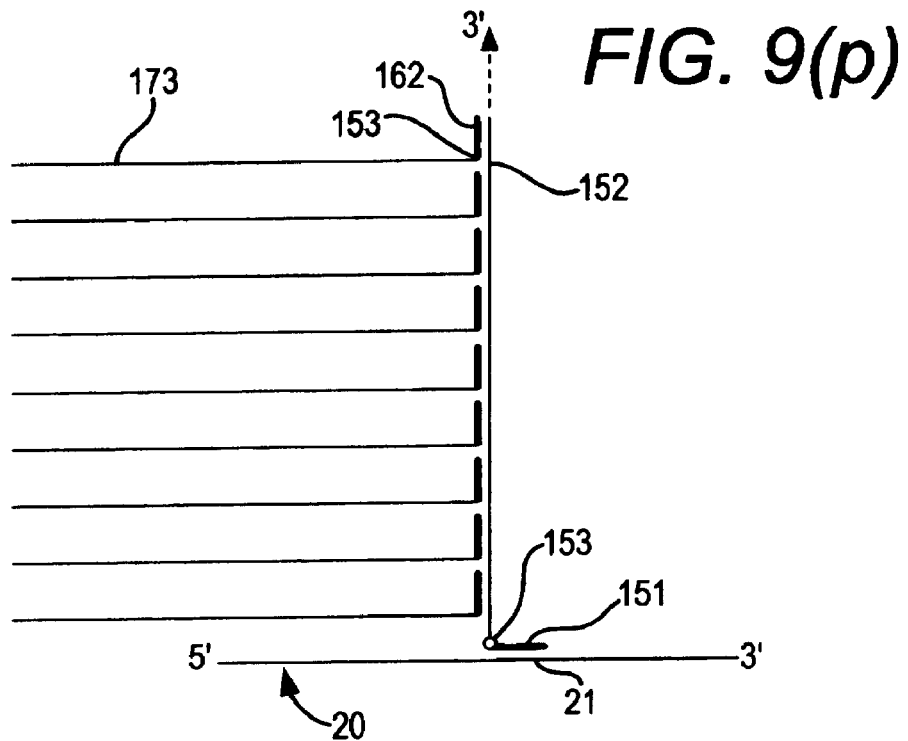
Figure 9Q:
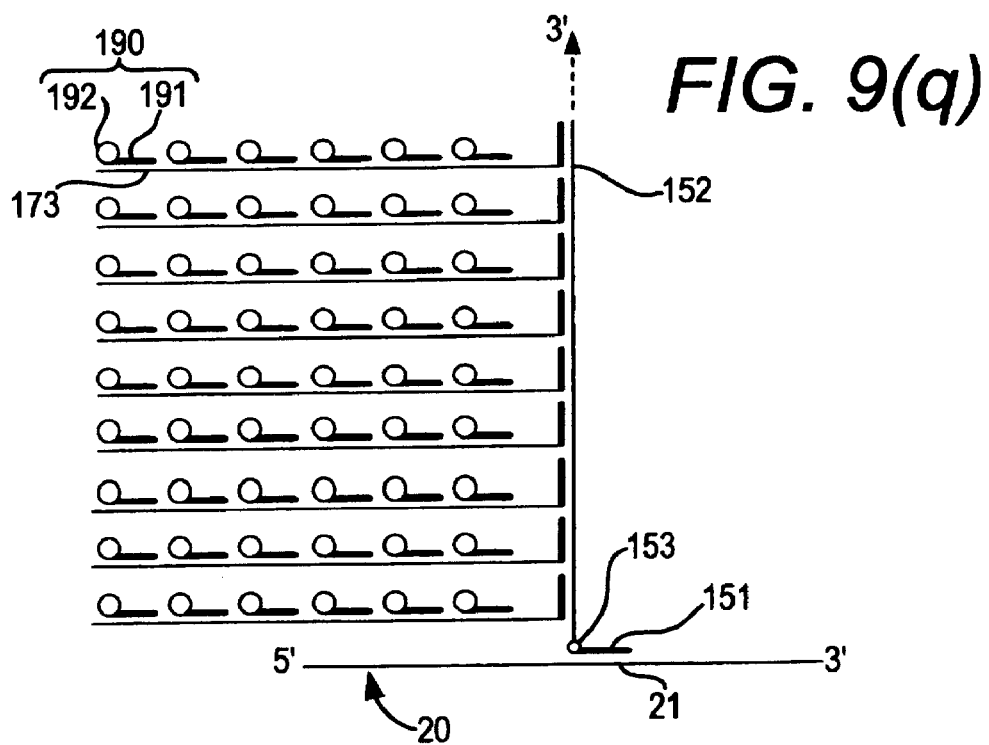

Once amplification moiety 152 has been sufficiently extended, it can be detected by hybridisation of Detection probes complementary to the repeats within the extended strand. Alternatively, secondary amplification templates, comprised in the 5'-3' direction of hybridisation region 161, extension blocker 153, and amplification moiety 173 are hybridised to extended amplification moiety 152 (FIGS. 9*i*, 9*j*). The hybridisation region can, if required, incorporate modified nucleotides (as in this example) to render it resistant to 5' double stranded exonuclease activity.

Amplification moiety 173 is then used as the target for an additional round of signal amplification performed as before using amplification template 180 comprised in the 5'-3' direction of hybridisation region 181 and extension region 182 (FIGS. 9*j*-9*p*). A final signal detection step is then performed (FIG. 9*q*) which detects the extension region 181 of amplification template 180.

EXAMPLE 5

The various embodiments (above) of the invention are modified insofar as extension nucleic acid sequences 41,52, 71,81,121,162 and 182 are provided in the form, of a loop motif. As a result the nucleotides within the loop motifs are unavailable for hybridisation to complementary nucleotides, for example in amplification nucleic acid sequences.

Thus the loop motifs prevent undesirable hybridisation of the extension nucleic acid sequences, the sequences only being exposed when the loop motif is linearised, i.e. by the action of a polymerizing agent such as DNA polymerase as it synthesizes a complementary strand to the extension nucleic acid sequence.

EXAMPLE 6

Concerted action of T7 gene 6 exonuclease and Klenow (exo-) polymerase.

CMV-002 (SEQ ID NO: 2), a 24-mer sequence specific for a conserved region in the GlyB gene of CMV, was covalently linked to solid phase support and used as the target for the Amplification Template SA-EX1 (SEQ ID NO: 3). A Detection Oligonucleotide SA-B1 (SEQ ID NO: 4) was designed to hybridise to the site generated by SA-EX1 in combination with the concerted action of Klenow (exo-) polymerase and T7 gene 6 exonuclease.

Nucleotides 1 and 2 of SEQ ID NO: 3 contain phosphorothioate linkages. Nucleotides 20–26 of SEQ ID NO: 3 are 2'-O-Methyl RNA. Nucleotide 1 of SEQ ID NO: 4 has a biotin label attached. All oligos were supplied by Oswel (Southampton UK).

76 pmoles of SA-EX1 was added to 2 mg of CMV-002 support in each of four 0.2 ml eppendorf tubes in a total volume of 40 ml of 1× Klenow (exo-) buffer. Hybridisation was allowed to proceed at room temperature for 10 minutes with gentle mixing by inversion at 1 minute intervals.

To tubes A and B, 10 ml of 1× Klenow buffer containing 10 units of Klenow (exo-) polymerase, 100 units of T7 gene 6 exonuclease and 2 ml of a 20 mM dNTP mix was added. To tube C, 10 ml of the same mixture omitting the polymerase was added, and to tube D, 10 ml of the mixture, omitting the T7 exonuclease was added. Samples were gently mixed and incubated at 37° C. for 15 minutes.

Samples were transferred to bottom fritted DARAS (RTM) columns (Tepnel Medical Limited, UK; www.tepnel.com). 100 ml of 1× Sample Buffer (50 mM Sodium citrate, 80 mM Sodium chloride, 8 mM Magnesium chloride, 10 mM Tris.HCl pH 8.3) was dispensed through each column in triplicate.

50 ml of 1× Sample Buffer containing 79 pmoles of SA-B1 was added to each column and the column contents mixed by periodic inversion for 10 minutes at room temperature. Columns were washed by passage of 100 ml of System Buffer (10 mM Tris.HCl, pH 8.3) through each in triplicate.

Figure 10:
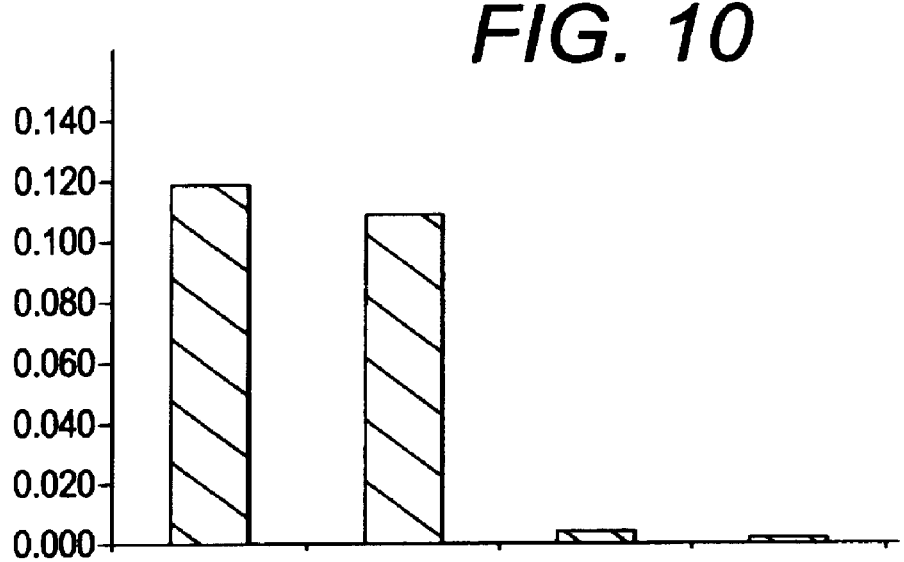
FIG. 10 shows results from Example 6. Y-axis shows slope (A490/minute) from 0 (bottom) to 0.140 (top). X-axis shows (left to right) Positive 1, Positive 2, Negative Klenow and Negative T7.

The presence of hybridised SA-B1 oligonucleotide was confirmed using the EDSA1 detect protocol on the DARAS (RTM) system. Results are presented in FIG. 10 as the slope of the signal detected (absorbance change at 490 nm/minute).

EXAMPLE 7

Strand extension by sequential hybridisation.

CMV-002 (SEQ ID NO: 2) was covalently linked to solid phase support and used as the target for the EDSA Amplification oligonucleotide SA-EX1 (SEQ ID NO: 3). A second Amplification Oligonucleotide, SA-EX22 (SEQ ID NO: 5), was designed to hybridise to the site generated by SA-EX1 through the concerted action of Klenow (exo-) polymerase and T7 exonuclease. A Detection oligonucleotide SA-B2 (SEQ ID NO: 6) was designed to hybridise to the site generated by SA-EX22 through the concerted action of Klenow (exo-) polymerase and T7 exonuclease.

Nucleotides 1 and 2 of SEQ ID NO: 5 contain phosphorothioate linkages. Nucleotides 22–27 of SEQ ID NO: 5 are 2'-O-Methyl RNA. Nucleotide 1 of SEQ ID NO: 6 has a biotin label attached. All oligos were supplied by Oswel (Southampton UK). All enzymes and buffers were supplied by Amersham Life Sciences Inc.(UK)

10 pmoles of SA-EX1 was added to 2 mg of CMV-002 support in each of six 0.2 ml eppendorf tubes in a total volume of 30 ml of 1× Klenow (exo-) buffer (50 mM Tris-HCl, pH 7.5, 10 mM $MgCl_2$, 1 mM DTT 50 mg/ml BSA). Hybridisation was allowed to proceed at room temperature for 10 minutes, with gentle mixing by inversion at one minute intervals. The solution phase was removed by aspiration, and 50 ml of 1× Klenow Buffer added. After the beads settled, the upper phase was removed by aspiration. This was repeated two more times.

To tubes A–E, 30 ml of 1× Klenow buffer containing 15 units of Klenow (exo-) polymerase, 100 units of T7 gene 6 exonuclease, 2 ml of a 20 mM dNTP mix and 100 pmoles of SA-EX22 was added. To tube F, 30 ml of the same mixture omitting both the polymerase and the T7 exonuclease was added. Samples were gently mixed and incubated at 37° C. for 30 minutes.

Samples were transferred to bottom fritted DARAS (RTM) columns. 100 ml of 1× Sample Buffer (50 mM Sodium citrate, 80 mM Sodium chloride, 8 mM Magnesium chloride, 10 mM Tris.HCl pH 8.3) was dispensed through each column in triplicate.

50 ml of 1× Sample Buffer containing 1 pmoles of SA-B2 was added to each column and the column contents mixed by periodic inversion for 10 minutes at room temperature. Columns were washed by passage of 100 ml of System Buffer (10 mM Tris.HCl, pH 8.3) through each in triplicate.

Figure 11:
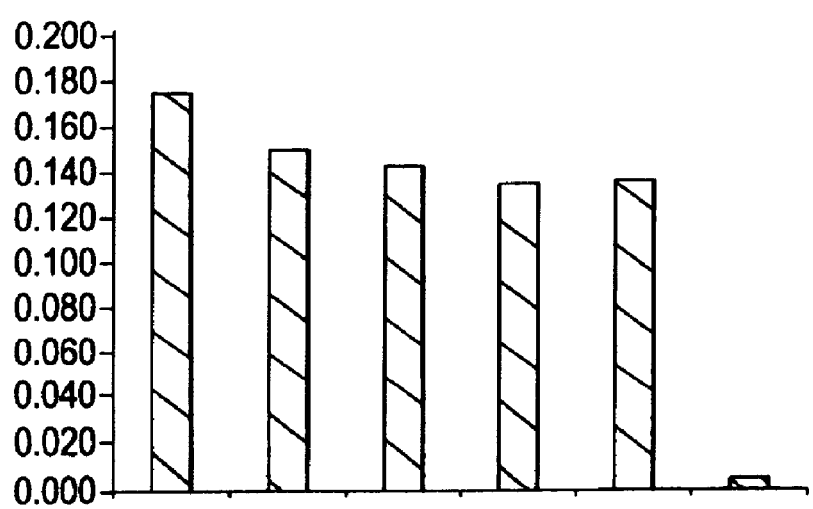
FIG. 11 shows strand extension by SAEX1 and SAEX22. Y-axis shows slope (A490/minute) from 0 (bottom) to 0.200 (top). X-axis shows (far-right) control with no enzyme and (all other columns) positives.

The presence of labelled SA-B2 oligonucleotide was confirmed using the EDSA1 detect protocol on the DARAS (RTM) system. Results are presented in FIG. 11 as the slope of the signal detected (absorbance change at 490 nm/minute).

What is claimed is:

1. A method of detecting a target molecule, comprising the steps of:
   i) contacting a sample with a locator probe comprising a binding moiety specific for the target molecule and an amplification nucleic acid sequence to produce a target molecule-locator probe complex;
   ii) producing an amplification structure bound to the complex by performing one or more times an amplification step of treating the sample and locator probe with:
      a) a single stranded amplification template comprising:
         i) arranged in a 5' to 3' direction:
            a) an extension nucleic acid sequence;
            b) a hybridisation nucleic acid sequence complementary to the amplification nucleic acid sequence having substantially the same sequence as the extension nucleic acid sequence; and
            c) an amplification moiety, being limited in all but the final repeat to a nucleic acid sequence; and
         ii) optionally comprising at least one signal moiety being other than a nucleic acid sequence;
      b) a polymerising agent which extends the 3' terminus of the amplification nucleic acid sequence by synthesising a complementary strand to the extension nucleic acid sequence of the amplification template;
      c) a separating agent which removes sufficient of the extension nucleic acid sequence of the amplification template when hybridised to the complementary strand to allow subsequent hybridisation of the hybridisation nucleic acid sequence of the amplification template to the complementary strand; and
      d) the reagents and conditions necessary to effect the action of the polymerising agent and separating agent to allow the extension of the 3' terminus of the amplification nucleic acid sequence by the synthesis of a plurality of sequences complementary to the extension nucleic acid sequence of the amplification template;
   iii) detecting any bound amplification template from the amplification step or steps; and
   iv) correlating the results of the detection step with the presence of the target molecule.

2. A method for detecting target molecule according to claim 1, wherein the separating agent is a 5' double stranded exonuclease, the activity against which the hybridisation nucleic acid sequence is protected.

3. A method for detecting a target molecule comprising the steps of:
   i) contacting a sample with a locator probe comprising a binding moiety specific for the target molecule and an amplification nucleic acid sequence to produce a target molecule-locator probe complex;
   ii) producing an amplification structure bound to any complex produced in the preceding step by performing one or more times the amplification step of treating the sample and locator probe with:
      a) a single stranded first amplification template comprising:
         i) arranged in a 5' to 3' direction:
            a) an extension nucleic acid sequence;
            b) a hybridisation nucleic acid sequence complementary to the amplification nucleic acid sequence having a substantially different sequence to the extension nucleic acid sequence; and
            c) an amplification moiety, being limited in all but the final repeat to a nucleic acid sequence; and ii) optionally comprising at least one signal moiety being other than a nucleic acid sequence;

b) a single stranded second amplification template comprising:
i) arranged in a 5' to 3' direction'
a) an extension nucleic acid sequence comprising the hybridisation nucleic acid sequence of the first amplification template;
b) a hybridisation nucleic acid sequence comprising the extension nucleic acid sequence of the first amplification template; and
c) an amplification moiety, being limited in all but the final amplification step to a nucleic acid sequence; and
ii) optionally comprising at least one signal moiety being other than a nucleic acid sequence;

c) a polymerising agent which extends the 3' terminus of the amplification nucleic acid sequence by synthesising a complementary strand to the extension nucleic acid sequence of the first and second amplification templates;

d) a separating agent which removes sufficient of the extension nucleic acid sequence of the first and second amplification templates when hybridised to the complementary strand to allow subsequent hybridisation of the hybridisation nucleic acid sequence of the first and second amplification templates to the complementary strand; and e) the reagents and conditions necessary to effect the action of the polymerising agent and separating agent to allow the extension of the 3' terminus of the amplification nucleic acid sequence by the synthesis of a plurality of sequences complementary to the extension nucleic acid sequences of the first and second amplification templates;

iii) detecting any bound first and/or second amplification template from the amplification step or steps; and iv) correlating the results of the detection step (iii) with the presence of the target molecule.

4. A method of detecting a target molecule according to claim 3, wherein the separating agent is a 5' double-stranded exonuclease, the activity against which the hybridisation nucleic acid sequence of said the first amplification template and the hybridisation nucleic acid sequence of the second amplification template are protected.

5. A method for detecting a target molecule comprising the steps of:
i) contacting a sample with a locator probe comprising a binding moiety specific for the target molecule and an amplification nucleic acid sequence to produce a target molecule-locator probe complex, the amplification nucleic acid sequence having one or more restriction sites for a restriction endonuclease when hybridised to a complementary strand;
ii) producing an amplification structure bound to any complex by performing one or more times the amplification step of treating the sample and locator probe with:
a) a single stranded amplification template comprising:
i) arranged in a 5' to 3' direction:
a) an extension nucleic acid sequence;
b) a hybridisation nucleic acid sequence complementary to the amplification nucleic acid sequence and having substantially the same sequence as the extension nucleic acid sequence; and c) an amplification moiety, being limited in all but the final amplification step to a nucleic acid sequence; and
ii) optionally comprising at least one signal moiety being other than a nucleic acid sequence;
b) a polymerising agent which extends the 3' terminus of the amplification nucleic acid sequence by synthesising a complementary strand to the extension nucleic acid sequence of the amplification template;
c) the restriction endonuclease; and
d) the reagents and conditions necessary to:
i) effect the action of the polymerising agent and a separating agent to allow the extension of the 3' terminus of the amplification nucleic acid sequence by the synthesis of a plurality of sequences complementary to the extension nucleic acid sequence of the amplification template; and
ii) effect dissociation of fragments of nucleic acid strands which have been cut by the restriction endonuclease activity from uncut complementary strands whilst not effecting dissociation of uncut nucleic acid strands from uncut complementary strands;
iii) detecting any bound amplification template from the amplification step or steps; and
iv) correlating the results of the detection step (iii) with the presence of the target molecule.

6. A method according to claim 5, the amplification nucleic acid sequence and the hybridisation nucleic acid sequence having nucleotide modifications which prevent cleavage by the restriction endonuclease, and the reagents including at least one modified nucleotide which, when incorporated into the complementary strand by the polymerising agent, prevent cleavage of the complementary strand by the restriction endonuclease.

7. A method according to claim 5, wherein the hybridisation nucleic acid sequence has at least one nucleotide modification which prevents cleavage by the restriction endonuclease, the restriction endonuclease having single stranded nicking activity only.

8. A method according to claim 5, wherein the method is performed isothermally.

9. A method according to claim 5, wherein the method is performed at more than one temperature.

10. A method according to claim 1, wherein the amplification step of step (ii) is performed two or more times.

11. A method for detecting a target molecule comprising the steps of:
i) contacting a sample with a locator probe comprising:
a) a binding moiety specific for the target molecule;
b) an amplification nucleic acid sequence to produce a target molecule-locator probe complex; and
c) optionally comprising a signal moiety being other than a nucleic acid sequence;
ii) producing an amplification structure bound to the complex by performing one or more times the amplification step of treating the complex with:
a) a single stranded amplification template comprising:
i) arranged in a 5' to 3' direction:
a) an extension nucleic acid sequence (162,182); and
b) a hybridisation nucleic acid sequence (161,181) complementary to the amplification nucleic acid sequence having substantially the same sequence as the extension nucleic acid sequence; and
ii) optionally comprising at least one signal moiety being other than a nucleic acid sequence;

b) a polymerising agent which extends the 3' terminus of the amplification nucleic acid sequence by synthesising a complementary strand to the extension nucleic acid sequence of the amplification template;
c) a separating agent which removes sufficient of the extension nucleic acid sequence of the amplification template when hybridised to the complementary strand to allow subsequent hybridisation of the hybridisation nucleic acid sequence of the amplification template to the complementary strand;
d) the reagents and conditions necessary to effect the action of the polymerising agent and separating agent to allow the extension of the 3' terminus of the amplification nucleic acid sequence by the synthesis of a plurality of sequences complementary to the extension nucleic acid sequence of the amplification template; and iii) optionally repeating one or more times the steps of treating the amplification structure with:
a) a separating agent which removes the remainder of the hybridisation nucleic acid sequence of the amplification template when hybridised to the complementary strand;
b) an additional locator probe comprising:
i) a hybridisation nucleic acid probe specific to the complementary strand; and
ii) an amplification moiety, being limited in all but the final repeat to a nucleic acid sequence; to produce a complex; and
c) performing the amplification step, optionally using an amplification template different to that which was previously used;

iv) detecting any bound additional locator probes or amplification template from the amplification step or steps; and v) correlating the results of the detection step (iv) with the presence of the target molecule.

12. A method for detecting a target molecule comprising the steps of:
i) contacting a sample with a locator probe comprising a binding moiety specific for the target molecule and an amplification nucleic acid sequence to produce a target molecule-locator probe complex;
ii) producing an amplification structure bound to the complex by performing one or more times the amplification step of treating the complex with:
a) a single stranded first amplification template comprising:
i) arranged in a 5' to 3' direction:
a) an extension nucleic acid sequence; and
b) a hybridisation nucleic acid sequence complementary to the amplification nucleic acid sequence having substantially the same sequence as the extension nucleic acid sequence; and
ii) optionally comprising at least one signal moiety being other than a nucleic acid sequence;
b) a single stranded second amplification template comprising:
i) arranged in a 5' to 3' direction:
a) an extension nucleic acid sequence comprising the first amplification template hybridisation nucleic acid sequence; and
b) a hybridisation nucleic acid sequence comprising the first amplification template extension nucleic acid sequence; and
ii) optionally comprising at least one signal moiety being other than a nucleic acid sequence;
c) a polymerising agent which extends the 3' terminus of the amplification nucleic acid sequence by synthesising a complementary strand to the extension nucleic acid sequence of the amplification template;
d) a separating agent which removes sufficient of the extension nucleic aid sequence of the first and second amplification templates when hybridised to the complementary strand to allow subsequent hybridisation of the hybridisation nucleic acid sequence of the first and second amplification templates to the complementary strand;
e) the reagents and conditions necessary to effect the action of the polymerising agent and separating agent to allow the extension of the 3' terminus of the amplification nucleic acid sequence by the synthesis of a plurality of sequences complementary to the extension nucleic acid sequence of the amplification template;

iii) optionally repeating one or more times the steps of treating the amplification structure with:
a) a separating agent which removes the remainder of the hybridisation nucleic acid sequences of the first and second amplification templates when hybridised to the complementary strand;
b) an additional locator probe comprising:
i) a hybridisation nucleic acid probe specific to the complementary strand; and
ii) an amplification moiety, being limited in all but the final repeat to a nucleic acid sequence to produce a complex;
c) performing the amplification step, optionally using an amplification template other that the first or second amplification templates;

iv) detecting any bound additional locator probes or amplification template from the amplification step or steps; and v) correlating the results of the detection step (iv) with the presence of the target molecule.

13. A method for detecting a target molecule according to claim 11, wherein the removal of the amplification template is achieved by the use of a 5' double strand specific exonuclease.

14. A method for detecting a target molecule according to claim 11, wherein the removal of the amplification template is achieved through the use of elevated temperature.

15. A method for detecting a target molecule according to claim 14, wherein the locator probe is covalently attached to the target molecule prior to the removal of the amplification template.

16. A method for detecting a target molecule according to claim 1, prior to said detection step further comprising the amplification step according to steps (ii) and (iii) of claim 11.

17. A method for detecting a target molecule according to claim 1, wherein the amplification moiety of the amplification template from the final amplification step comprising a nucleic acid sequence, and prior to the detection step further comprising the amplification step according to steps (ii)–(iii) of a claim 11.

18. A method for detecting a target molecule according to claim 11, prior to the detection step further comprising the amplification step according to step (ii) of claim 1.

19. A method for detecting a target molecule according to claim 11, the amplification moiety of the locator probe or additional locator probe from the final amplification step comprising a nucleic acid sequence, and prior to the detection step further comprising an amplification step according to step (ii) of a claim 1.

20. A method for detecting a target molecule according to claim 1, wherein the step of detecting any bound amplification template further comprises the steps of:
   i) treating the sample, locator probe and amplification template or amplification templates with a detection probe which binds specifically to the amplification moiety of the last of the amplification templates; and
   ii) detecting any bound detection probe.

21. A method for detecting a target molecule according to claim 12, wherein the step of detecting any bound amplification template further comprises the steps of:
   i) treating the sample, locator probe and amplification template with a detection probe which binds specifically to the amplification moiety of the last of the amplification templates; and
   ii) detecting any bound detection probe.

22. A method according to claim 20, wherein the detection probe has a label which is detected by any one of the group of luminometry, fluorometry, spectrophotometry, and radiometry.

23. A method according to claim 22, wherein the detection probe is labelled with any one of the group of, FAM (carboxyfluorescein), HEX (hexachlorofluorescein), TET (tetrachlorofluorescein), ROX (carboxy-X-rhodamine), TAMRA (carboxytetramethylrhodamine), JOE (carboxy-4', 5'-dichloro-2',7'-dimethoxyfluorescein), or with biotin.

24. A method according to claim 1, wherein the amplification step is performed two or more times, each amplification step being performed using an amplification template having a different extension nucleic acid sequence, hybridisation nucleic acid sequence and amplification moiety to that of the amplification template used in the previous amplification step.

25. A method according to claim 1, wherein the target molecule to be detected is a nucleic acid sequence and the binding moiety of the locator probe comprising a nucleic acid sequence complementary to the target molecule nucleic acid sequence.

26. A method according to claim 1, wherein the method is performed using more than one locator probe, each locator probe having the same amplification nucleic acid sequence.

27. A method according to claim 1, wherein the method further comprises two repeats.

28. A method according to claim 1, wherein unreacted reagents are removed by washing.

29. A method according to claim 28, wherein the unreacted reagents are selected from the group of locator probe, amplification template, and detection probe.

30. A method according to claim 3, wherein the amplification step is performed two or more times.

31. A method according to claim 5, wherein the amplification step is performed two or more times.

32. A method for detecting a target molecule according to claim 12, wherein the removal of the amplification template is achieved by the use of a 5' double strand specific exonuclease.

33. A method for detecting a target molecule according to claim 12, wherein the removal of the amplification template is achieved through the use of elevated temperature.

34. A method according to claim 21, wherein the detection probe having a label is detected by any one of the group of luminometry, fluorometry, spectrophotometry, and radiometry.

35. A method according to claim 34, wherein the detection probe is labelled with any one of the group of, FAM (carboxyfluorescein), HEX (hexachlorofluorescein), TET (tetrachlorofluorescein), ROX (carboxy-X-rhodamine), TAMRA (carboxytetramethylrhodamine), JOE (carboxy-4', 5'-dichloro-2',7'-dimethoxyfluorescein), or with biotin.

36. A method for detecting a target molecule according to claim 3, wherein prior to the detection step further comprising the amplification steps (ii) and (iii) of claim 11.

37. A method for detecting a target molecule according to claim 5, wherein prior to the detection step further comprising the amplification steps (ii) and (iii) of claim 11.

38. A method for detecting a target molecule according to claim 1, wherein prior to the detection step further comprising the amplification steps (ii) and (iii) of claim 12.

39. A method for detecting a target molecule according to claim 3, wherein prior to the detection step further comprising the amplification steps (ii) and (iii) of claim 12.

40. A method for detecting a target molecule according to claim 5, wherein prior to the detection step further comprising the amplification steps (ii) and (iii) of claim 12.

41. A method for detecting a target molecule according to claim 12, wherein prior to the detection step further comprising the amplification step (ii) of claim 1.

42. A method for detecting a target molecule according to claim 11, wherein prior to the detection step further comprising the amplification step (ii) of claim 3.

43. A method for detecting a target molecule according to claim 12, wherein prior to the detection step further comprising the amplification step (ii) of claim 3.

44. A method for detecting a target molecule according to claim 11, wherein prior to the detection step further comprising the amplification step (ii) of claim 5.

45. A method for detecting a target molecule according to claim 12, wherein prior to the detection step further comprising the amplification step (ii) of claim 5.

46. A method for detecting a target molecule according to claim 12, wherein the amplification moiety of the locator probe or additional locator probe from the final amplification step comprising a nucleic acid sequence, and prior to the detection step further comprising the amplification step (ii) of claim 1.

47. A method for detecting a target molecule according to claim 11, wherein the amplification moiety of the locator probe or additional locator probe from the final amplification step comprising a nucleic acid sequence, and prior to the detection step further comprising the amplification step (ii) of claim 3.

48. A method for detecting a target molecule according to claim 12, wherein the amplification moiety of the locator probe or additional locator probe from the final amplification step comprising a nucleic acid sequence, and prior to the detection step further comprising the amplification step (ii) of claim 3.

49. A method for detecting a target molecule according to claim 11, wherein the amplification moiety of the locator probe or additional locator probe from the final amplification step comprising a nucleic acid sequence, and prior to the detection step further comprising the amplification step (ii) of claim 5.

50. A method for detecting a target molecule according to claim 12, wherein the amplification moiety of the locator probe or additional locator probe from the final amplification step comprising a nucleic acid sequence, and prior to the detection step further comprising the amplification step (ii) of claim 5.

51. A method for detecting a target molecule according to claim 3, the step of detecting any bound amplification template comprising the steps of:
   i) treating the sample, locator probe and amplification template or amplification templates with a detection probe which binds specifically to the amplification moiety of the amplification templates; and
   ii) detecting any bound detection probe.

52. A method for detecting a target molecule according to claim 5, the step of detecting any bound amplification template comprising the steps of:
   i) treating the sample, locator probe and amplification template or amplification templates with a detection probe which binds specifically to the amplification moiety of the amplification templates; and
   ii) detecting any bound detection probe.

53. A method for detecting a target molecule according to claim 18, the step of detecting any bound amplification template comprising the steps of:
   i) treating the sample, locator probe and amplification template or amplification templates with a detection probe which binds specifically to the amplification moiety of the amplification templates; and
   ii) detecting any bound detection probe.

54. A method for detecting a target molecule according to claim 19, the step of detecting any bound amplification template comprising the steps of:
   i) treating the sample, locator probe and amplification template or amplification templates with a detection probe which binds specifically to the amplification moiety of the last of said amplification templates; and
   ii) detecting any bound detection probe.

55. A method for detecting a target molecule according to claim 12, the step of detecting any bound amplification template comprising the steps of:
   i) treating the sample, locator probe and amplification template with a detection probe which binds specifically to the amplification moiety of the amplification templates; and
   ii) detecting any bound detection probe.

56. A method according to claim 3, wherein the amplification step is performed two or more times, each amplification step being performed using an amplification template having a different extension nucleic acid sequence, hybridisation nucleic acid sequence and amplification moiety to that of the amplification template used in the previous amplification step.

57. A method according to claim 5, wherein the amplification step is performed two or more times, each amplification step being performed using an amplification template having a different extension nucleic acid sequence, hybridisation nucleic acid sequence and amplification moiety to that of the amplification template used in the previous amplification step.

58. A method according to claim 11, wherein the amplification step is performed two or more times, each amplification step being performed using an amplification template having a different extension nucleic acid sequence, hybridisation nucleic acid sequence and amplification moiety to that of the amplification template used in the previous amplification step.

59. A method according to claim 12, wherein the amplification step is performed two or more times, each amplification step being performed using an amplification template having a different extension nucleic acid sequence, hybridisation nucleic acid sequence and amplification moiety to that of the amplification template used in the previous amplification step.

60. A method according to claim 3, wherein the target molecule to be detected is a nucleic acid sequence and the binding moiety of the locator probe comprising a nucleic acid sequence complementary to the target molecule nucleic acid sequence.

61. A method according to claim 5, wherein the target molecule to be detected is a nucleic acid sequence and the binding moiety of the locator probe comprises a nucleic acid sequence complementary to the target molecule nucleic acid sequence.

62. A method according to claim 11, wherein the target molecule to be detected is a nucleic acid sequence and the binding moiety of the locator probe comprises a nucleic acid sequence complementary to the target molecule nucleic acid sequence.

63. A method according to claim 12, wherein the target molecule to be detected is a nucleic acid sequence and the binding moiety of the locator probe comprises a nucleic acid sequence complementary to the target molecule nucleic acid sequence.

64. A method according to claim 3, wherein the method is performed using more than one locator probe, each locator probe having the same amplification nucleic acid sequence.

65. A method according to claim 5, wherein the method is performed using more than one locator probe, each locator probe having the same amplification nucleic acid sequence.

66. A method according to claim 11, wherein the method is performed using more than one locator probe, each locator probe having the same amplification nucleic acid sequence.

67. A method according to claim 12, wherein the method is performed using more than one locator probe, each locator probe having the same amplification nucleic acid sequence.

68. A method according to claim 3, further comprising two repeats of the amplication step.

69. A method according to claim 5, further comprising two repeats of the amplication step.

70. A method according to claim 11, further comprising two repeats of the amplication step.

71. A method according to claim 12, further comprising two repeats of the amplication step.

72. A method according to claim 3, wherein unreacted reagents are removed at the end of step (i), each repeat, of the amplication step or detection step by washing.

73. A method according to claim 72, wherein the unreacted reagents are selected from the group of locator probe, amplification template, and detection probe.

74. A method according to claim 5, wherein unreacted reagents are removed at the end of step (i), each repeat, of the amplication step or detection step by washing.

75. A method according to claim 74, wherein the unreacted reagents are selected from the group of locator probe, amplification template, and detection probe.

76. A method according to claim 11, wherein unreacted reagents are removed at the end step (i), each repeat, of the amplication step or detection step by washing.

77. A method according to claim 76, wherein the unreacted reagents are selected from the group of locator probe, amplification template, and detection probe.

78. A method according to claim 12, wherein unreacted reagents are removed at the end of step (i), each repeat, of the amplication step or detection step by washing.

79. A method according to claim 78, wherein the unreacted reagents are selected from the group of locator probe, amplification template, and detection probe.

* * * * *

SEQUENCE LISTING

```
<160> NUMBER OF SEQ ID NOS: 6

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: N.BstNB1
      recognition sequence
<220> FEATURE:
<221> NAME/KEY: misc_feature
<222> LOCATION: (6)..(10)
<223> OTHER INFORMATION: Any nucleotide - N.BstNB1 recognition sequence

<400> SEQUENCE: 1 gagtcnnnnn                                                          10

<210> SEQ ID NO 2
<211> LENGTH: 24
<212> TYPE: DNA
<213> ORGANISM: Cytomegalovirus
<220> FEATURE:
<223> OTHER INFORMATION: Description of Combined DNA/RNA Molecule:
```

-continued

Endonuclease protected sequence
<400> SEQUENCE: 2
tcgacggtgg agatactgct gagg                                        24

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence:
      Amplification template
<220> FEATURE:
<221> NAME/KEY: modified_base
<222> LOCATION: (20)
<223> OTHER INFORMATION: cm
<220> FEATURE:
<221> NAME/KEY: modified_base
<222> LOCATION: (21)
<223> OTHER INFORMATION: um
<220> FEATURE:
<221> NAME/KEY: modified_base
<222> LOCATION: (22)
<223> OTHER INFORMATION: cm
<220> FEATURE:
<221> NAME/KEY: misc_feature
<222> LOCATION: (23)
<223> OTHER INFORMATION: 2'-O-methyladenosine
<220> FEATURE:
<221> NAME/KEY: modified_base
<222> LOCATION: (24)
<223> OTHER INFORMATION: gm
<220> FEATURE:
<221> NAME/KEY: modified_base
<222> LOCATION: (25)
<223> OTHER INFORMATION: cm
<220> FEATURE:
<221> NAME/KEY: misc_feature
<222> LOCATION: (26)
<223> OTHER INFORMATION: 2'-O-methyladenosine

<400> SEQUENCE: 3
ttctccttcc agttgctacc ucagcagtat ctccac                           36

<210> SEQ ID NO 4
<211> LENGTH: 18
<212> TYPE: DNA
<213> ORGANISM: Artificial Sequence
<220> FEATURE:
<223> OTHER INFORMATION: Description of Combined DNA/RNA Molecule:
      Endonuclease protected sequence
<220> FEATURE:
<223> OTHER INFORMATION: Description of Artificial Sequence: Detection
      oligonucleotide

<400> SEQUENCE: 4
ttctccttcc agttgcta                                               18

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence:
      Amplification template
<220> FEATURE:
<221> NAME/KEY: modified_base
<222> LOCATION: (22)
<223> OTHER INFORMATION: cm
<220> FEATURE:
<221> NAME/KEY: modified_base
<222> LOCATION: (23)
<223> OTHER INFORMATION: um

```
-continued

<220> FEATURE:
<221> NAME/KEY: modified_base
<222> LOCATION: (24)
<223> OTHER INFORMATION: um
<220> FEATURE:
<221> NAME/KEY: modified_base
<222> LOCATION: (25)
<223> OTHER INFORMATION: cm
<220> FEATURE:
<221> NAME/KEY: modified_base
<222> LOCATION: (26)
<223> OTHER INFORMATION: cm
<220> FEATURE:
<221> NAME/KEY: misc_feature
<222> LOCATION: (27)
<223> OTHER INFORMATION: 2'-O-methyladenosine

<400> SEQUENCE: 5
gtgaagatgt tgcatgttct ccuuccagtt gctacc                                36

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Detection
      oligonucleotide

<400> SEQUENCE: 6
gtgaagatgt tgcatgtt                                                    18
```